United States Patent [19]
Nickias et al.

[11] Patent Number: 6,015,868
[45] Date of Patent: *Jan. 18, 2000

[54] SUBSTITUTED INDENYL CONTAINING METAL COMPLEXES AND OLEFIN POLYMERIZATION PROCESS

[75] Inventors: Peter N. Nickias; Mark H. McAdon; Jasson T. Patton, all of Midland, Mich.; Bernard P. Friedrichsen, Madison, Wis.; Jorge Soto, Midland, Mich.; James C. Stevens, Richmond; Daniel D. VanderLende, Sugar Land, both of Tex.

[73] Assignee: The Dow Chemical Company, Midland, Mich.

[ * ] Notice: This patent is subject to a terminal disclaimer.

[21] Appl. No.: 09/011,895

[22] PCT Filed: Oct. 3, 1996

[86] PCT No.: PCT/US96/16012

§ 371 Date: Feb. 19, 1998

§ 102(e) Date: Feb. 19, 1998

[87] PCT Pub. No.: WO97/15583

PCT Pub. Date: May 1, 1997

[51] Int. Cl.[7] ............. C08F 4/643; C07F 17/00; B01J 31/00
[52] U.S. Cl. ............. 526/127; 556/11; 556/13; 556/19; 556/20; 556/52; 556/53; 526/130; 526/134; 526/160; 526/943; 502/103; 502/117
[58] Field of Search .................. 556/11, 13, 19, 556/20, 52, 53; 502/103, 117; 526/127, 130, 134, 160, 943

[56] References Cited

U.S. PATENT DOCUMENTS

| | | | |
|---|---|---|---|
| 4,985,576 | 1/1991 | Rohrmann et al. | 556/435 |
| 5,026,798 | 6/1991 | Canich | 526/127 |
| 5,055,438 | 10/1991 | Canich | 502/117 |
| 5,057,475 | 10/1991 | Canich et al. | 502/104 |
| 5,064,802 | 11/1991 | Stevens et al. | 502/155 |
| 5,096,867 | 3/1992 | Canich | 502/103 |
| 5,132,380 | 7/1992 | Stevens et al. | 526/126 |
| 5,145,819 | 9/1992 | Winter et al. | 502/117 |
| 5,153,157 | 10/1992 | Hlatky et al. | 502/117 |
| 5,278,264 | 1/1994 | Spaleck et al. | 526/127 |
| 5,329,033 | 7/1994 | Spaleck et al. | 556/53 |
| 5,495,036 | 2/1996 | Wilson et al. | 556/12 |
| 5,688,880 | 11/1997 | Spencer et al. | 526/127 |
| 5,866,704 | 2/1999 | Nickias et al. | 556/11 |

FOREIGN PATENT DOCUMENTS

| | | |
|---|---|---|
| 277 003 | 8/1988 | European Pat. Off. . |
| 416 815 | 3/1991 | European Pat. Off. . |
| 468 651 | 1/1992 | European Pat. Off. . |
| 514 828 | 11/1992 | European Pat. Off. . |
| 520 732 | 12/1992 | European Pat. Off. . |
| 576970 | 1/1994 | European Pat. Off. . |
| WO 93/19104 | 9/1993 | WIPO . |
| WO 95/00526 | 1/1995 | WIPO . |
| WO 95/14024 | 5/1995 | WIPO . |

OTHER PUBLICATIONS

*Organometallics*, 13, pp. 954–963, 1994.
Organometallics, 15, pp. 2450–2453, 1996.

*Primary Examiner*—Porfirio Nazario-Gonzalez

[57] ABSTRACT

Group 4 metal complexes comprising an indenyl group substituted in the 2 or 3 position with at least one group selected from hydrocarbyl, fluoro-substituted hydrocarbyl, hydrocarbyloxy-substituted hydrocarbyl, dialkylamino-substituted hydroacrbyl, silyl, germyl and mixtures thereof, said indenyl group further being covalently bonded to the metal by means of a divalent ligand group, catalytic derivatives thereof and their use as olefin polymerization catalysts are disclosed.

21 Claims, No Drawings

SUBSTITUTED INDENYL CONTAINING METAL COMPLEXES AND OLEFIN POLYMERIZATION PROCESS

This invention relates to class of Group 4 metal complexes and to olefin polymerization catalysts derived therefrom that are particularly suitable for use in a polymerization process for preparing polymers by polymerization of α-olefins and mixtures of α-olefins.

Constrained geometry metal complexes and methods for their preparation are disclosed in EP-A-416,815; EP-A-468,651; EP-A-514,828; EP-A-520,732 and WO93/19104, as well as U.S. Pat. Nos. 5,055,438, 5,057,475, 5,096,867, 5,064,802, 5,132,380, and WO95/00526.

According to the present invention there are provided metal complexes corresponding to the formula:

$$Z\ A'\ M\ X_pX'_q,$$

wherein:

M is titanium, zirconium or hafnium in the +2, +3 or +4 formal oxidation state;

A' is a substituted indenyl group substituted in at least the 2 or 3 position with a group selected from hydrocarbyl, fluoro-substituted hydrocarbyl, hydrocarbyloxy-substituted hydrocarbyl, dialkylamino-substituted hydrocarbyl, silyl, germyl and mixtures thereof, said group containing up to 40 nonhydrogen atoms, and said A' further being covalently bonded to M by means of a divalent Z group;

Z is a divalent moiety bound to both A' and M via σ-bonds, said Z comprising boron, or a member of Group 14 of the Periodic Table of the Elements, and also comprising nitrogen, phosphorus, sulfur or oxygen;

X is an anionic or dianionic ligand group having up to 60 atoms exclusive of the class of ligands that are cyclic, delocalized, π-bound ligand groups;

X' independently each occurrence is a neutral Lewis base ligating compound, having up to 20 atoms;

p is 0, 1 or 2 and is two less than the formal oxidation state of M, with the proviso that when X is a dianionic ligand group, p is 1; and q is 0, 1 or 2.

The above complexes may exist as isolated crystals optionally in pure form or as a mixture with other complexes, in the form of a solvated adduct, optionally in a solvent, especially an organic liquid, as well as in the form of a dimer or chelated derivative thereof, wherein the chelating agent is an organic material, preferably a neutral Lewis base, especially a trihydrocarbylamine, trihydrocarbylphosphine, or halogenated derivative thereof.

Further according to the present invention there is provided a process for preparing polymers of olefin monomers comprising contacting one or more such monomers with a catalyst comprising:

1) a metal complex corresponding to the formula:

$$Z\ A'\ M\ X_pX'_q,$$

wherein:

M is titanium, zirconium or hafnium in the +2, +3 or +4 formal oxidation state;

A' is a substituted indenyl group substituted in at least the 2 or 3 position with a group selected from hydrocarbyl, fluoro-substituted hydrocarbyl, hydrocarbyloxy-substituted hydrocarbyl, dialkylamino-substituted hydrocarbyl, silyl, germyl and mixtures thereof, said group containing up to 40 nonhydrogen atoms, and said A' further being covalently bonded to M by means of a divalent Z group;

Z is a divalent moiety bound to both A' and M via σ-bonds, said z comprising boron, or a member of Group 14 of the Periodic Table of the Elements, and also comprising nitrogen, phosphorus, sulfur or oxygen;

X is an anionic or dianionic ligand group having up to 60 atoms exclusive of the class of ligands that are cyclic, delocalized, π-bound ligand groups;

X' independently each occurrence is a neutral Lewis base ligating compound, having up to 20 atoms;

p is 0, 1 or 2 and is two less than the formal oxidation state of M, with the proviso that when X is a dianionic ligand group, p is 1; and q is 0, 1 or 2: and 2) an activating cocatalyst the molar ratio of 1) to 2) being from 1:10,000 to 100:1, or the reaction product formed by converting 1) to an active catalyst by use of an activating technique.

The present catalysts and process result in the highly efficient production of high molecular weight olefin polymers over a wide range of polymerization conditions, and especially at elevated temperatures. They are especially useful for the solution polymerization of ethylene/propylene (EP polymers) and ethylene/propylene/diene (EPDM polymers) wherein the diene is ethylidenenorbornene, 1,4-hexadiene or similar nonconjugated diene. The use of elevated temperatures dramatically increases the productivity of such process due to the fact that increased polymer solubility at elevated temperatures allows the use of increased conversions (higher concentration of polymer product) without exceeding solution viscosity limitations of the polymerization equipment as well as reduced energy costs needed to devolatize the reaction product.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Olefins as used herein are $C_{2-20}$ aliphatic or aromatic compounds containing vinylic unsaturation, as well as cyclic compounds such as cyclobutene, cyclopentene, and norbornene, including norbornene substituted in the 5 and 6 position with C1-20 hydrocarbyl groups. Also included are mixtures of such olefins as well as mixtures of such olefins with $C_{4-40}$ diolefin compounds. Examples of the latter compounds include ethylidene norbornene, 1,4-hexadiene, norbornadiene, and the like. The catalysts and process herein are especially suited for use in preparation of ethylene/1-butene, ethylene/1-hexene, ethylene/styrene, and ethylene/1-octene copolymers as well as terpolymers of ethylene, propylene and a nonconjugated diene, that is EPDM terpolymers.

Preferred X' groups are carbon monoxide; phosphines, especially trimethylphosphine, triethylphosphine, iophenylphosphine and bis(1,2-dimethylphosphino)ethane; $P(OR)_3$, wherein R is as previously defined ethers, especially tetrahydrofuran; amines, especially pyridine, bidyridine, tetramethylethylenediamine (TMEDA), and triethylamine; olefins; and conjugated dienes having from 4 to 40 carbon atoms. Complexes including the latter X' groups include those wherein the metal is in the +2 formal oxidation state.

Preferred coordination complexes used according to the present invention are complexes corresponding to the formula:

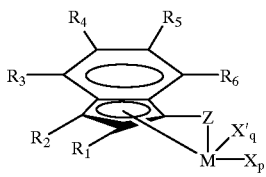

wherein:

$R_1$ and $R_2$, independently are groups selected from hydrogen, hydrocarbyl, perfluoro substituted hydrocarbyl, silyl, germyl and mixtures thereof, said group containing up to 20 nonhydrogen atoms, with the proviso that at least one of $R_1$ or $R_2$ is not hydrogen;

$R_3$, $R_4$, $R_5$, and $R_6$ independently are groups selected from hydrogen, hydrocarbyl, perfluoro substituted hydrocarbyl, silyl, germyl and mixtures thereof, said group containing up to 20 nonhydrogen atoms;

M is titanium, zirconium or hafnium;

Z is a divalent moiety comprising boron, or a member of Group 14 of the Periodic Table of the Elements, and also comprising nitrogen, phosphorus, sulfur or oxygen, said moiety having up to 60 non-hydrogen atoms;

p is 0, 1 or 2;

q is zero or one;

with the proviso that:

when p is 2, q is zero, M is in the +4 formal oxidation state, and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)phosphino-substituted derivatives thereof, said X group having up to 20 nonhydrogen atoms, when p is 1, q is zero, M is in the +3 formal oxidation state, and X is a stabilizing anionic ligand group selected from the group consisting of allyl, 2-(N,N-dimethylaminomethyl)phenyl, and 2-(N,N-dimethyl)-aminobenzyl, or M is in the +4 formal oxidation state, and X is a divalent derivative of a conjugated diene, M and X together forming a metallocyclopentene group, and when p is 0, q is 1, M is in the +2 formal oxidation state, and X' is a neutral, conjugated or nonconjugated diene, optionally substituted with one or more hydrocarbyl groups, said X' having up to 40 carbon atoms and forming a π-complex with M.

More preferred coordination complexes used according to the present invention are complexes corresponding to the formula:

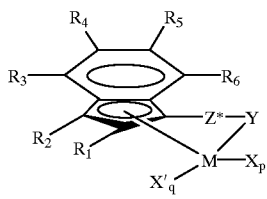

wherein:

$R_1$ and $R_2$ are hydrogen or $C_{1-6}$ alkyl, with the proviso that at least one of $R_1$ or $R_2$ is not hydrogen;

$R_3$, $R_4$, $R_5$, and $R_6$ independently are hydrogen or $C_{1-6}$ alkyl;

M is titanium;

Y is —O—, —S—, —NR*—, —PR*—;

$Z^*$ is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$;

$R^*$ each occurrence is independently hydrogen, or a member selected from hydrocarbyl, hydrocarbyloxy, silyl, halogenated alkyl, halogenated aryl, and combinations thereof, said $R^*$ having up to 20 non-hydrogen atoms, and optionally, two $R^*$ groups from Z (when $R^*$ is not hydrogen), or an $R^*$ group from Z and an $R^*$ group from Y form a ring system;

p is 0, 1 or 2;

q is zero or one;

with the proviso that:

when p is 2, q is zero, M is in the +4 formal oxidation state, and X is independently each occurrence methyl or benzyl, when p is 1, q is zero, M is in the +3 formal oxidation state, and X is 2-(N,N-dimethyl)aminobenzyl: or M is in the +4 formal oxidation state and X is 1,4-butadienyl, and when p is 0, q is 1, M is in the +2 formal oxidation state, and X' is 1,4-diphenyl-1,3-butadiene or 1,3-pentadiene. The latter diene is illustrative of unsymetrical diene groups that result in production of metal complexes that are actually mixtures of the respective geometrical isomers.

Highly preferred metal complexes are:

2-methylindenyl complexes:
(t-butylamido)dimethyl($\eta^5$-2-methylindenyl)silanetitanium (II) 1,4-diphenyl-1,3-butadiene,
(t-butylamido)dimethyl($\eta^5$-2-methylindenyl)silanetitanium (II) 1,3-pentadiene,
(t-butylamido)dimethyl($\eta^5$-2-methylindenyl)silanetitanium (III) 2-(N,N-dimethylamino)benzyl,
(t-butylamido)dimethyl($\eta^5$-2-methylindenyl)silanetitanium (IV) dimethyl,
(t-butylamido)dimethyl($\eta^5$-2-methylindenyl)silanetitanium (IV) dibenzyl,
(n-butylamido)dimethyl($\eta^5$-2-methylindenyl)silanetitanium (II) 1,4-diphenyl-1,3-butadiene,
(n-butylamido)dimethyl($\eta^5$-2-methylindenyl)silanetitanium (II) 1,3-pentadiene,
(n-butylamido)dimethyl($\eta^5$-2-methylindenyl)silanetitanium (III) 2-(N,N-dimethylamino)benzyl,
(n-butylamido)dimethyl($\eta^5$-2-methylindenyl)silanetitanium (IV) dimethyl,
(n-butylamido)dimethyl($\eta^5$-2-methylindenyl)silanetitanium (IV) dibenzyl,
(cyclododecylamido)dimethyl($\eta^5$-2-methylindenyl)silanetitanium (II) 1,4-diphenyl-1,3-butadiene,
(cyclododecylamido)dimethyl($\eta^5$-2-methylindenyl)silanetitanium (II) 1,3-pentadiene,
(cyclododecylamido)dimethyl($\eta^5$-2-methylindenyl)silanetitanium (III) 2-(N,N-dimethylamino)benzyl,
(cyclododecylamido)dimethyl($\eta^5$-2-methylindenyl)silanetitanium (IV) dimethyl,
(cyclododecylamido)dimethyl($\eta^5$-2-methylindenyl)silanetitanium (IV dibenzyl,
(2,4,6-trimethylamilido)dimethyl($\eta^5$-2-methylindenyl)silanetitanium (II) 1,4-diphenyl-1,3-butadiene,
(2,4,6-trimethylamilido)dimethyl($\eta^5$-2-methylindenyl)silanetitanium (II) 1,3-pentadiene,
(2,4,6-trimethylamilido)dimethyl($\eta^5$-2-methylindenyl)silanetitanium (III) 2-(N,N-dimethylamino)benzyl,
(2,4,6-trimethylamilido)dimethyl($\eta^5$-2-methylindenyl)silanetitanium (IV) dimethyl,
(2,4,6-trimethylamilido)dimethyl($\eta^5$-2-methylindenyl)silanetitanium (IV) dibenzyl, (1-adamantylamido)dimethyl($\eta^5$-2-methylindenyl) silanetitanium (II) 1,4-diphenyl-1,3-butadiene,
(1-adamantylamido)dimethyl($\eta^5$-2-methylindenyl) silanetitanium (II) 1,3-pentadiene,
(1-adamantylamido)dimethyl($\eta^5$-2-methylindenyl) silanetitanium (III) 2-(N,N-dimethylamino)benzyl,
(1-adamantylamido)dimethyl($\eta^5$-2-methylindenyl) silanetitanium (IV) dimethyl,
(1-adamantylamido)dimethyl($\eta^5$-2-methylindenyl) silanetitanium (IV) dibenzyl,
(n-butylamido)diisopropoxy($\eta^5$-2-methylindenyl) silanetitanium (II) 1,4-diphenyl-1,3-butadiene,
(n-butylamido)diisopropoxy($\eta^5$-2-methylindenyl) silanetitanium (II) 1,3-pentadiene,
(n-butylamido)diisopropoxy($\eta^5$-2-methylindenyl) silanetitanium (III) 2-(N,N-dimethylamino)benzyl,
(n-butylamido)diisopropoxy($\eta^5$-2-methylindenyl) silanetitanium (IV) dimethyl,
(n-butylamido)diisopropoxy($\eta^5$-2-methylindenyl) silanetitanium (IV) dibenzyl,
(cyclododecylamido)diisopropoxy($\eta^5$-2-methylindenyl)- silanetitanium (II) 1,4-diphenyl-1,3-butadiene,
(cyclododecylamido)diisopropoxy($\eta^5$-2-methylindenyl)- silanetitanium (II) 1,3-pentadiene,
(cyclododecylamido)diisopropoxy($\eta^5$-2-methylindenyl)- silanetitanium ((III) 2-(N,N-dimethylamino)benzyl,
(cyclododecylamido)diisopropoxy($\eta^5$-2-methylindenyl)- silanetitanium (IV) dimethyl,
(cyclododecylamido)diisopropoxy($\eta^5$-2-methylindenyl)- silanetitanium (IV) dibenzyl,
(2,4,6-trimethylanilido)diisopropoxy($\eta^5$-2-methyl-indenyl) silanetitanium (II) 1,4-diphenyl-1,3-butadiene,
(2,4,6-trimethylanilido)diisopropoxy($\eta^5$-2-methylindenyl) silanetitanium (II) 1,3-pentadiene,
(2,4,6-trimethylanilido)diisopropoxy($\eta^5$-2-methylin-denyl) silanetitanium (III) 2-(N,N-dimethylamino)benzyl,
(2,4,6-trimethylanilido)diisopropoxy($\eta^5$-2-methylindenyl) silanetitanium (IV) dimethyl,
(2,4,6-trimethylanilido)diisopropoxy($\eta^5$-2-methyl-indenyl) silanetitanium (IV) dibenzyl,
(1-adamantylamido)diisopropoxy($\eta^5$-2-methylindenyl) silanetitanium (II) 1,4-diphenyl-1,3-butadiene,
(1-adamantylamido)diisopropoxy($\eta^5$-2-methylindenyl) silanetitanium (II) 1,3-pentadiene,
(1-adamantylamido)diisopropoxy($\eta^5$-2-methylindenyl) silanetitanium (III) 2-(N,N-dimethylamino)benzyl,
(1-adamantylamido)diisopropoxy($\eta^5$-2-methylindenyl) silanetitanium (IV) dimethyl,
(1-adamantylamido)diisopropoxy($\eta^5$-2-methylindenyl) silanetitanium (IV) dibenzyl,
(n-butylamido)dimethoxy($\eta^5$-2-methylindenyl) silanetitanium (II) 1,4-diphenyl-1,3-butadiene,
(n-butylamido)dimethoxy($\eta^5$-2-methylindenyl) silanetitanium (II) 1,3-pentadiene,
(n-butylamido)dimethoxy($\eta^5$-2-methylindenyl) silanetitanium (III) 2-(N,N-dimethylamino)benzyl,
(n-butylamido)dimethoxy($\eta^5$-2-methylindenyl) silanetitanium (IV) dimethyl,
(n-butylamido)dimethoxy($\eta^5$-2-methylindenyl) silanetitanium (IV) dibenzyl,
(cyclododecylamido)dimethoxy($\eta^5$-2-methylindenyl) silanetitanium (II) 1,4-diphenyl-1,3-butadiene,
(cyclododecylamido)dimethoxy($\eta^5$-2-methylindenyl) silanetitanium (II) 1,3-pentadiene,
(cyclododecylamido)dimethoxy($\eta^5$-2-methylindenyl) silanetitanium (III) 2-(N,N-dimethylamino)benzyl,
(cyclododecylamido)dimethoxy($\eta^5$-2-methylindenyl) silanetitanium (IV) dimethyl,
(cyclododecylamido)dimethoxy($\eta^5$-2-methylindenyl) silanetitanium (IV) dibenzyl,
(2,4,6-trimethylanilido)dimethoxy($\eta^5$-2-methylindenyl) silanetitanium (II) 1,4-diphenyl-1,3-butadiene,
(2,4,6-trimethylanilido)dimethoxy($\eta^5$-2-methylindenyl) silanetitanium (II) 1,3-pentadiene,
(2,4,6-trimethylanilido)dimethoxy($\eta^5$-2-methylindenyl) silanetitanium (III) 2-(N,N-dimethylamino)benzyl,
(2,4,6-trimethylanilido)dimethoxy($\eta^5$-2-methylindenyl) silanetitanium (IV) dimethyl,
(2,4,6-trimethylanilido)dimethoxy($\eta^5$-2-methylindenyl) silanetitanium (IV) dibenzyl,
(1-adamantylamido)dimethoxy($\eta^5$-2-methylindenyl) silanetitanium (II) 1,4-diphenyl-1,3-butadiene,
(1-adamantylamido)dimethoxy($\eta^5$-2-methylindenyl) silanetitanium (II) 1,3-pentadiene,
(1-adamantylamido)dimethoxy($\eta^5$-2-methylindenyl) silanetitanium (III) 2-(N,N-dimethylamino)benzyl,
(1-adamantylamido)dimethoxy($\eta^5$-2-methylindenyl) silanetitanium (IV) dimethyl,
(1-adamantylamido)dimethoxy($\eta^5$-2-methylindenyl) silanetitanium (IV) dibenzyl,
(n-butylamido)ethoxymethyl($\eta^5$-2-methylindenyl) silanetitanium (II) 1,4-diphenyl-1,3-butadiene,
(n-butylamido)ethoxymethyl($\eta^5$-2-methylindenyl) silanetitanium (II) 1,3-pentadiene,
(n-butylamido)ethoxymethyl($\eta^5$-2-methylindenyl) silanetitanium (III) 2-(N,N-dimethylamino)benzyl,
(n-butylamido)ethoxymethyl($\eta^5$-2-methylindenyl) silanetitanium (IV) dimethyl,
(n-butylamido)ethoxymethyl($\eta^5$-2-methylindenyl) silanetitanium (IV) dibenzyl,
(cyclododecylamido)ethoxymethyl($\eta^5$-2-methylindenyl) silanetitanium (II) 1,4-diphenyl-1,3-butadiene,
(cyclododecylamido)ethoxymethyl($\eta^5$-2-methylindenyl) silanetitanium (II) 1,3-pentadiene,
(cyclododecylamido)ethoxymethyl($\eta^5$-2-methylindenyl) silanetitanium (III) 2-(N,N-dimethylamino)benzyl,
(cyclododecylamido)ethoxymethyl($\eta^5$-2-methylindenyl) silanetitanium (IV) dimethyl,
(cyclododecylamido)ethoxymethyl($\eta^5$-2-methylindenyl) silanetitanium (IV) dibenzyl,
(2,4,6-trimethylanilido)ethoxymethyl($\eta^5$-2-methylindenyl) silanetitanium (II) 1,4-diphenyl-1,3-butadiene,
(2,4,6-trimethylanilido)ethoxymethyl($\eta^5$-2-methylindenyl) silanetitanium (II) 1,3-pentadiene,
(2,4,6-trimethylanilido)ethoxymethyl($\eta^5$-2-methylindenyl) silanetitanium (III) 2-(N,N-dimethylamino)benzyl,
(2,4,6-trimethylanilido)ethoxymethyl($\eta^5$-2-methylindenyl) silanetitanium (IV) dimethyl,
(2,4,6-trimethylanilido)ethoxymethyl($\eta^5$-2-methylindenyl) silanetitanium (IV) dibenzyl,
(1-adamantylamido)ethoxymethyl($\eta^5$-2-methylindenyl) silanetitanium (II) 1,4-diphenyl-1,3-butadiene,
(1-adamantylamido)ethoxymethyl($\eta^5$-2-methylindenyl) silanetitanium (II) 1,3-pentadiene,
(1-adamantylamido)ethoxymethyl($\eta^5$-2-methylindenyl) silanetitanium (III) 2-(N,N-dimethylamino)benzyl,
(1-adamantylamido)ethoxymethyl($\eta^5$-2-methylindenyl) silanetitanium (IV) dimethyl,
(1-adamantylamido)ethoxymethyl($\eta^5$-2-methylindenyl) silanetitanium (IV) dibenzyl,
2,3-dimethylindenyl complexes:
(t-butylamido)dimethyl($\eta^5$-2,3-dimethylindenyl) silanetitanium (II) 1,4-diphenyl-1,3-butadiene,
(t-butylamido)dimethyl($\eta^5$-2,3-dimethylindenyl) silanetitanium (II) 1,3-pentadiene, (t-butylamido)dimethyl($\eta^5$-2,3-dimethylindenyl)silanetitanium (III) 2-(N,N-dimethylamino)benzyl,
(t-butylamido)dimethyl($\eta^5$-2,3-dimethylindenyl)silanetitanium (IV) dimethyl,
(t-butylamido)dimethyl($\eta^5$-2,3-dimethylindenyl)silanetitanium (IV) dibenzyl,
(n-butylamido)dimethyl($\eta^5$-2,3-dimethylindenyl)silanetitanium (II) 1,4-diphenyl-1,3-butadiene,
(n-butylamido)dimethyl($\eta^5$-2,3-dimethylindenyl)silanetitanium (II) 1,3-pentadiene,
(n-butylamido)dimethyl($\eta^5$-2,3-dimethylindenyl)silanetitanium (III) 2-(N,N-dimethylamino)benzyl,
(n-butylamido)dimethyl($\eta^5$-2,3-dimethylindenyl)silanetitanium (IV) dimethyl,
(n-butylamido)dimethyl($\eta^5$-2,3-dimethylindenyl)silanetitanium (IV) dibenzyl,
(cyclododecylamido)dimethyl($\eta^5$-2,3-dimethylindenyl)silanetitanium (II) 1,4-diphenyl-1,3-butadiene,
(cyclododecylamido)dimethyl($\eta^5$-2,3-dimethylindenyl)silanetitanium (II) 1,3-pentadiene,
(cyclododecylamido)dimethyl($\eta^5$-2,3-dimethylindenyl)silanetitanium (III) 2-(N,N-dimethylamino)benzyl,
(cyclododecylamido)dimethyl($\eta^5$-2,3-dimethylindenyl)silanetitanium (IV) dimethyl,
(cyclododecylamido)dimethyl($\eta^5$-2,3-dimethylindenyl)silanetitanium (IV dibenzyl,
(2,4,6-trimethylamilido)dimethyl($\eta^5$-2,3-dimethylindenyl)silanetitanium (II) 1,4-diphenyl-1,3-butadiene,
(2,4,6-trimethylamilido)dimethyl($\eta^5$-2,3-dimethylindenyl)silanetitanium (II) 1,3-pentadiene,
(2,4,6-trimethylamilido)dimethyl($\eta^5$-2,3-dimethylindenyl)silanetitanium (III) 2-(N,N-dimethylamino)benzyl,
(2,4,6-trimethylamilido)dimethyl($\eta^5$-2,3-dimethylindenyl)silanetitanium (IV) dimethyl,
(2,4,6-trimethylamilido)dimethyl($\eta^5$-2,3-dimethylindenyl)silanetitanium (IV) dibenzyl,
(1-adamantylamido)dimethyl($\eta^5$-2,3-dimethylindenyl)silanetitanium (II) 1,4-diphenyl-1,3-butadiene,
(1-adamantylamido)dimethyl($\eta^5$-2,3-dimethylindenyl)silanetitanium (II) 1,3-pentadiene,
(1-adamantylamido)dimethyl($\eta^5$-2,3-dimethylindenyl)silanetitanium (III) 2-(N,N-dimethylamino)benzyl,
(1-adamantylamido)dimethyl($\eta^5$-2,3-dimethylindenyl)silanetitanium (IV) dimethyl,
(1-adamantylamido)dimethyl($\eta^5$-2,3-dimethylindenyl)silanetitanium (IV) dibenzyl,
(n-butylamido)diisopropoxy($\eta^5$-2,3-dimethylindenyl)silanetitanium (II) 1,4-diphenyl-1,3-butadiene,
(n-butylamido)diisopropoxy($\eta^5$-2,3-dimethylindenyl)silanetitanium (II) 1,3-pentadiene,
(n-butylamido)diisopropoxy($\eta^5$-2,3-dimethylindenyl)silanetitanium (III) 2-(N,N-dimethylamino)benzyl,
(n-butylamido)diisopropoxy($\eta^5$-2,3-dimethylindenyl)silanetitanium (IV) dimethyl,
(n-butylamido)diisopropoxy($\eta^5$-2,3-dimethylindenyl)silanetitanium (IV) dibenzyl,
(cyclododecylamido)diisopropoxy($\eta^5$-2,3-dimethylindenyl)-silanetitanium (II) 1,4-diphenyl-1,3-butadiene,
(cyclododecylamido)diisopropoxy($\eta^5$-2,3-dimethylindenyl)-silanetitanium (II) 1,3-pentadiene,
(cyclododecylamido)diisopropoxy($\eta^5$-2,3-dimethylindenyl)-silanetitanium ((III) 2-(N,N-dimethylamino)benzyl,
(cyclododecylamido)diisopropoxy($\eta^5$-2,3-dimethylindenyl)-silanetitanium (IV) dimethyl,
(cyclododecylamido)diisopropoxy($\eta^5$-2,3-dimethylindenyl)-silanetitanium (IV) dibenzyl,
(2,4,6-trimethylanilido)diisopropoxy($\eta^5$(2,3-dimethylindenyl)silanetitanium (II) 1,4-diphenyl-1,3-butadiene,
(2,4,6-trimethylanilido)diisopropoxy($\eta^5$(2,3-dimethylindenyl)silanetitanium (II) 1,3-pentadiene,
(2,4,6-trimethylanilido)diisopropoxy($\eta^5$(2,3-dimethylindenyl)silanetitanium (III) 2-(N,N-dimethylamino)benzyl,
(2,4,6-trimethylanilido)diisopropoxy($\eta^5$(2,3-dimethylindenyl)silanetitanium (IV) dimethyl,
(2,4,6-trimethylanilido)diisopropoxy($\eta^5$(2-methyl-indenyl)silanetitanium (IV) dibenzyl,
(1-adamantylamido)diisopropoxy($\eta^5$-2,3-dimethylindenyl)silanetitanium (II) 1,4-diphenyl-1,3-butadiene,
(1-adamantylamido)diisopropoxy($\eta^5$-2,3-dimethylindenyl)silanetitanium (II) 1,3-pentadiene,
(1-adamantylamido)diisopropoxy($\eta^5$-2,3-dimethylindenyl)silanetitanium (III) 2-(N,N-dimethylamino)benzyl,
(1-adamantylamido)diisopropoxy($\eta^5$-2,3-dimethylindenyl)silanetitanium (IV) dimethyl,
(1-adamantylamido)diisopropoxy($\eta^5$-2,3-dimethylindenyl)silanetitanium (IV) dibenzyl,
(n-butylamido)dimethoxy($\eta^5$-2,3-dimethylindenyl)silanetitanium (II) 1,4-diphenyl-1,3-butadiene,
(n-butylamido)dimethoxy($\eta^5$-2,3-dimethylindenyl)silanetitanium (II) 1,3-pentadiene,
(n-butylamido)dimethoxy($\eta^5$-2,3-dimethylindenyl)silanetitanium (III) 2-(N,N-dimethylamino)benzyl,
(n-butylamido)dimethoxy($\eta^5$-2,3-dimethylindenyl)silanetitanium (IV) dimethyl,
(n-butylamido)dimethoxy($\eta^5$-2,3-dimethylindenyl)silanetitanium (IV) dibenzyl,
(cyclododecylamido)dimethoxy($\eta^5$-2,3-dimethylindenyl)silanetitanium (II) 1,4-diphenyl-1,3-butadiene,
(cyclododecylamido)dimethoxy($\eta^5$-2,3-dimethylindenyl)silanetitanium (II) 1,3-pentadiene,
(cyclododecylamido)dimethoxy($\eta^5$-2,3-dimethylindenyl)silanetitanium (III) 2-(N,N-dimethylamino)benzyl,
(cyclododecylamido)dimethoxy($\eta^5$-2,3-dimethylindenyl)silanetitanium (IV) dimethyl,
(cyclododecylamido)dimethoxy($\eta^5$-2,3-dimethylindenyl)silanetitanium (IV) dibenzyl,
(2,4,6-trimethylanilido)dimethoxy($\eta^5$-2,3-dimethylindenyl)silanetitanium (II) 1,4-diphenyl-1,3-butadiene,
(2,4,6-trimethylanilido)dimethoxy($\eta^5$-2,3-dimethylindenyl)silanetitanium (II) 1,3-pentadiene,
(2,4,6-trimethylanilido)dimethoxy($\eta^5$-2,3-dimethylindenyl)silanetitanium (III) 2-(N,N-dimethylamino)benzyl,
(2,4,6-trimethylanilido)dimethoxy($\eta^5$-2,3-dimethylindenyl)silanetitanium (IV) dimethyl,
(2,4,6-trimethylanilido)dimethoxy($\eta^5$-2,3-dimethylindenyl)silanetitanium (IV) dibenzyl,
(1-adamantylamido)dimethoxy($\eta^5$-2,3-dimethylindenyl)silanetitanium (II) 1,4-diphenyl-1,3-butadiene,
(1-adamantylamido)dimethoxy($\eta^5$-2,3-dimethylindenyl)silanetitanium (II) 1,3-pentadiene,
(1-adamantylamido)dimethoxy($\eta^5$-2,3-dimethylindenyl)silanetitanium (III) 2-(N,N-dimethylamino)benzyl,
(1-adamantylamido)dimethoxy($\eta^5$-2,3-dimethylindenyl)silanetitanium (IV) dimethyl,
(1-adamantylamido)dimethoxy($\eta^5$-2,3-dimethylindenyl)silanetitanium (IV) dibenzyl,
(n-butylamido)ethoxymethyl($\eta^5$-2,3-dimethylindenyl)silanetitanium (II) 1,4-diphenyl-1,3-butadiene,
(n-butylamido)ethoxymethyl($\eta^5$-2,3-dimethylindenyl)silanetitanium (II) 1,3-pentadiene,
(n-butylamido)ethoxymethyl($\eta^5$-2,3-dimethylindenyl)silanetitanium (III) 2-(N,N-dimethylamino)benzyl,
(n-butylamido)ethoxymethyl($\eta^5$-2,3-dimethylindenyl)silanetitanium (IV) dimethyl, (n-butylamido)ethoxymethyl($\eta^5$-2,3-dimethylindenyl)
silanetitanium (IV) dibenzyl,
(cyclododecylamido)ethoxymethyl($\eta^5$-2,3-
dimethylindenyl)silanetitanium (II) 1,4-diphenyl-1,3-
butadiene,
(cyclododecylamido)ethoxymethyl($\eta^5$-2,3-
dimethylindenyl)silanetitanium (II) 1,3-pentadiene,
(cyclododecylamido)ethoxymethyl($\eta^5$-2,3-
dimethylindenyl)silanetitanium (III) 2-(N,N-
dimethylamino)benzyl,
(cyclododecylamido)ethoxymethyl($\eta^5$-2,3-
dimethylindenyl)silanetitanium (IV) dimethyl,
(cyclododecylamido)ethoxymethyl($\eta^5$-2,3-
dimethylindenyl)silanetitanium (IV) dibenzyl,
(2,4,6-trimethylanilido)ethoxymethyl($\eta^5$-2,3-
dimethylindenyl)silanetitanium (II) 1,4-diphenyl-1,3-
butadiene,
(2,4,6-trimethylanilido)ethoxymethyl($\eta^5$-2,3-
dimethylindenyl)silanetitanium (II) 1,3-pentadiene,
(2,4,6-trimethylanilido)ethoxymethyl($\eta^5$-2,3-
dimethylindenyl)silanetitanium (III) 2-(N,N-
dimethylamino)benzyl,
(2,4,6-trimethylanilido)ethoxymethyl($\eta^5$-2,3-
dimethylindenyl)silanetitanium (IV) dimethyl,
(2,4,6-trimethylanilido)ethoxymethyl($\eta^5$-2,3-
dimethylindenyl)silanetitanium (IV) dibenzyl,
(1-adamantylamido)ethoxymethyl($\eta^5$-2,3-dimethylindenyl)
silanetitanium (II) 1,4-diphenyl-1,3-butadiene,
(1-adamantylamido)ethoxymethyl($\eta^5$-2,3-dimethylindenyl)
silanetitanium (II) 1,3-pentadiene,
(1-adamantylamido)ethoxymethyl($\eta^5$-2,3-dimethylindenyl)
silanetitanium (III) 2-(N,N-dimethylamino)benzyl,
(1-adamantylamido)ethoxymethyl($\eta^5$-2,3-dimethylindenyl)
silanetitanium (IV) dimethyl,
(1-adamantylamido)ethoxymethyl($\eta^5$-2,3-dimethylindenyl)
silanetitanium (IV) dibenzyl, 3-methylindenyl complexes:
(t-butylamido)dimethyl($\eta^5$-3-methylindenyl)silanetitanium
(II) 1,4-diphenyl-1,3-butadiene,
(t-butylamido)dimethyl($\eta^5$-3-methylindenyl)silanetitanium
(II) 1,3-pentadiene,
(t-butylamido)dimethyl($\eta^5$-3-methylindenyl)silanetitanium
(III) 2-(N,N-dimethylamino)benzyl,
(t-butylamido)dimethyl($\eta^5$-3-methylindenyl)silanetitanium
(IV) dimethyl,
(t-butylamido)dimethyl($\eta^5$-3-methylindenyl)silanetitanium
(IV) dibenzyl,
(n-butylamido)dimethyl($\eta^5$-3-methylindenyl)silanetitanium
(II) 1,4-diphenyl-1,3-butadiene,
(n-butylamido)dimethyl($\eta^5$-3-methylindenyl)silanetitanium
(II) 1,3-pentadiene,
(n-butylamido)dimethyl($\eta^5$-3-methylindenyl)silanetitanium
(III) 2-(N,N-dimethylamino)benzyl,
(n-butylamido)dimethyl($\eta^5$-3-methylindenyl)silanetitanium
(IV) dimethyl,
(n-butylamido)dimethyl($\eta^5$-3-methylindenyl)silanetitanium
(IV) dibenzyl,
(cyclododecylamido)dimethyl($\eta^5$-3-methylindenyl)
silanetitanium (II) 1,4-diphenyl-1,3-butadiene,
(cyclododecylamido)dimethyl($\eta^5$-3-methylindenyl)
silanetitanium (II) 1,3-pentadiene,
(cyclododecylamido)dimethyl($\eta^5$-3-methylindenyl)
silanetitanium (III) 2-(N,N-dimethylamino)benzyl,
(cyclododecylamido)dimethyl($\eta^5$-3-methylindenyl)
silanetitanium (IV) dimethyl,
(cyclododecylamido)dimethyl($\eta^5$-3-methylindenyl)
silanetitanium (IV dibenzyl,
(2,4,6-trimethylamilido)dimethyl($\eta^5$-3-methylindenyl)
silanetitanium (II) 1,4-diphenyl-1,3-butadiene,
(2,4,6-trimethylamilido)dimethyl($\eta^5$-3-methylindenyl)
silanetitanium (II) 1,3-pentadiene,
(2,4,6-trimethylamilido)dimethyl($\eta^5$-3-methylindenyl)
silanetitanium (III) 2-(N,N-dimethylamino)benzyl,
(2,4,6-trimethylamilido)dimethyl($\eta^5$-3-methylindenyl)
silanetitanium (IV) dimethyl,
(2,4,6-trimethylamilido)dimethyl($\eta^5$-3-methylindenyl)
silanetitanium (IV) dibenzyl,
(1-adamantylamido)dimethyl($\eta^5$-3-methylindenyl)
silanetitanium (II) 1,4-diphenyl-1,3-butadiene,
(1-adamantylamido)dimethyl($\eta^5$-3-methylindenyl)
silanetitanium (II) 1,3-pentadiene,
(1-adamantylamido)dimethyl($\eta^5$-3-methylindenyl)
silanetitanium (III) 2-(N,N-dimethylamino)benzyl,
(1-adamantylamido)dimethyl($\eta^5$-3-methylindenyl)
silanetitanium (IV) dimethyl,
(1-adamantylamido)dimethyl($\eta^5$-3-methylindenyl)
silanetitanium (IV) dibenzyl,
(n-butylamido)diisopropoxy($\eta^5$-3-methylindenyl)
silanetitanium (II) 1,4-diphenyl-1,3-butadiene,
(n-butylamido)diisopropoxy($\eta^5$-3-methylindenyl)
silanetitanium (II) 1,3-pentadiene,
(n-butylamido)diisopropoxy($\eta^5$-3-methylindenyl)
silanetitanium (III) 2-(N,N-dimethylamino)benzyl,
(n-butylamido)diisopropoxy($\eta^5$-3-methylindenyl)
silanetitanium (IV) dimethyl,
(n-butylamido)diisopropoxy($\eta^5$-3-methylindenyl)
silanetitanium (IV) dibenzyl,
(cyclododecylamido)diisopropoxy($\eta^5$-3-methylindenyl)-
silanetitanium (II) 1,4-diphenyl-1,3-butadiene,
(cyclododecylamido)diisopropoxy($\eta^5$-3-methylindenyl)-
silanetitanium (II) 1,3-pentadiene,
(cyclododecylamido)diisopropoxy($\eta^5$-3-methylindenyl)-
silanetitanium ((III) 2-(N,N-dimethylamino)benzyl,
(cyclododecylamido)diisopropoxy($\eta^5$-3-methylindenyl)-
silanetitanium (IV) dimethyl,
(cyclododecylamido)diisopropoxy($\eta^5$-3-methylindenyl)-
silanetitanium (IV) dibenzyl,
(2,4,6-trimethylanilido)diisopropoxy($\eta^5$-3-methyl-indenyl)
silanetitanium (II) 1,4-diphenyl-1,3-butadiene,
(2,4,6-trimethylanilido)diisopropoxy($\eta^5$-3-methylindenyl)
silanetitanium (II) 1,3-pentadiene,
(2,4,6-trimethylanilido)diisopropoxy($\eta^5$-3-methylin-denyl)
silanetitanium (III) 2-(N,N-dimethylamino)benzyl,
(2,4,6-trimethylanilido)diisopropoxy($\eta^5$-3-methylindenyl)
silanetitanium (IV) dimethyl,
(2,4,6-trimethylanilido)diisopropoxy($\eta^5$-3-methyl-indenyl)
silanetitanium (IV) dibenzyl,
(1-adamantylamido)diisopropoxy($\eta^5$-3-methylindenyl)
silanetitanium (II) 1,4-diphenyl-1,3-butadiene,
(1-adamantylamido)diisopropoxy($\eta^5$-3-methylindenyl)
silanetitanium (II) 1,3-pentadiene,
(1-adamantylamido)diisopropoxy($\eta^5$-3-methylindenyl)
silanetitanium (III) 2-(N,N-dimethylamino)benzyl,
(1-adamantylamido)diisopropoxy($\eta^5$-3-methylindenyl)
silanetitanium (IV) dimethyl,
(1-adamantylamido)diisopropoxy($\eta^5$-3-methylindenyl)
silanetitanium (IV) dibenzyl,
(n-butylamido)dimethoxy($\eta^5$-3-methylindenyl)
silanetitanium (II) 1,4-diphenyl-1,3-butadiene,
(n-butylamido)dimethoxy($\eta^5$-3-methylindenyl)
silanetitanium (II) 1,3-pentadiene,
(n-butylamido)dimethoxy($\eta^5$-3-methylindenyl)
silanetitanium (III) 2-(N,N-dimethylamino)benzyl,
(n-butylamido)dimethoxy($\eta^5$-3-methylindenyl)
silanetitanium (IV) dimethyl, (n-butylamido)dimethoxy($\eta^5$-3-methylindenyl) silanetitanium (IV) dibenzyl,
(cyclododecylamido)dimethoxy($\eta^5$-3-methylindenyl) silanetitanium (II) 1,4-diphenyl-1,3-butadiene,
(cyclododecylamido)dimethoxy($\eta^5$-3-methylindenyl) silanetitanium (II) 1,3-pentadiene,
(cyclododecylamido)dimethoxy($\eta^5$-3-methylindenyl) silanetitanium (III) 2-(N,N-dimethylamino)benzyl,
(cyclododecylamido)dimethoxy($\eta^5$-3-methylindenyl) silanetitanium (IV) dimethyl,
(cyclododecylamido)dimethoxy($\eta^5$-3-methylindenyl) silanetitanium (IV) dibenzyl,
(2,4,6-trimethylanilido)dimethoxy($\eta^5$-3-methylindenyl) silanetitanium (II) 1,4-diphenyl-1,3-butadiene,
(2,4,6-trimethylanilido)dimethoxy($\eta^5$-3-methylindenyl) silanetitanium (II) 1,3-pentadiene,
(2,4,6-trimethylanilido)dimethoxy($\eta^5$-3-methylindenyl) silanetitanium (III) 2-(N,N-dimethylamino)benzyl,
(2,4,6-trimethylanilido)dimethoxy($\eta^5$-3-methylindenyl) silanetitanium (IV) dimethyl,
(2,4,6-trimethylanilido)dimethoxy($\eta^5$-3-methylindenyl) silanetitanium (IV) dibenzyl,
(1-adamantylamido)dimethoxy($\eta^5$-3-methylindenyl) silanetitanium (II) 1,4-diphenyl-1,3-butadiene,
(1-adamantylamido)dimethoxy($\eta^5$-3-methylindenyl) silanetitanium (II) 1,3-pentadiene,
(1-adamantylamido)dimethoxy($\eta^5$-3-methylindenyl) silanetitanium (III) 2-(N,N-dimethylamino)benzyl,
(1-adamantylamido)dimethoxy($\eta^5$-3-methylindenyl) silanetitanium (IV) dimethyl,
(1-adamantylamido)dimethoxy($\eta^5$-3-methylindenyl) silanetitanium (IV) dibenzyl,
(n-butylamido)ethoxymethyl($\eta^5$-3-methylindenyl) silanetitanium (II) 1,4-diphenyl-1,3-butadiene,
(n-butylamido)ethoxymethyl($\eta^5$-3-methylindenyl) silanetitanium (II) 1,3-pentadiene,
(n-butylamido)ethoxymethyl($\eta^5$-3-methylindenyl) silanetitanium (III) 2-(N,N-dimethylamino)benzyl,
(n-butylamido)ethoxymethyl($\eta^5$-3-methylindenyl) silanetitanium (IV) dimethyl,
(n-butylamido)ethoxymethyl($\eta^5$-3-methylindenyl) silanetitanium (IV) dibenzyl,
(cyclododecylamido)ethoxymethyl($\eta^5$-3-methylindenyl) silanetitanium (II) 1,4-diphenyl-1,3-butadiene,
(cyclododecylamido)ethoxymethyl($\eta^5$-3-methylindenyl) silanetitanium (II) 1,3-pentadiene,
(cyclododecylamido)ethoxymethyl($\eta^5$-3-methylindenyl) silanetitanium (III) 2-(N,N-dimethylamino)benzyl,
(cyclododecylamido)ethoxymethyl($\eta^5$-3-methylindenyl) silanetitanium (IV) dimethyl,
(cyclododecylamido)ethoxymethyl($\eta^5$-3-methylindenyl) silanetitanium (IV) dibenzyl,
(2,4,6-trimethylanilido)ethoxymethyl($\eta^5$-3-methylindenyl) silanetitanium (II) 1,4-diphenyl-1,3-butadiene,
(2,4,6-trimethylanilido)ethoxymethyl($\eta^5$-3-methylindenyl) silanetitanium (II) 1,3-pentadiene,
(2,4,6-trimethylanilido)ethoxymethyl($\eta^5$-3-methylindenyl) silanetitanium (III) 2-(N,N-dimethylamino)benzyl,
(2,4,6-trimethylanilido)ethoxymethyl($\eta^5$-3-methylindenyl) silanetitanium (IV) dimethyl,
(2,4,6-trimethylanilido)ethoxymethyl($\eta^5$-3-methylindenyl) silanetitanium (IV) dibenzyl,
(1-adamantylamido)ethoxymethyl($\eta^5$-3-methylindenyl) silanetitanium (II) 1,4-diphenyl-1,3-butadiene,
(1-adamantylamido)ethoxymethyl($\eta^5$-3-methylindenyl) silanetitanium (II) 1,3-pentadiene,
(1-adamantylamido)ethoxymethyl($\eta^5$-3-methylindenyl) silanetitanium (III) 2-(N,N-dimethylamino)benzyl,
(1-adamantylamido)ethoxymethyl($\eta^5$-3-methylindenyl) silanetitanium (IV) dimethyl,
(1-adamantylamido)ethoxymethyl($\eta^5$-3-methylindenyl) silanetitanium (IV) dibenzyl, 2-methyl-3-ethylindenyl complexes:
(t-butylamido)dimethyl($\eta^5$-2-methyl-3-ethylindenyl) silanetitanium (II) 1,4-diphenyl-1,3-butadiene,
(t-butylamido)dimethyl($\eta^5$-2-methyl-3-ethylindenyl) silanetitanium (II) 1,3-pentadiene,
(t-butylamido)dimethyl($\eta^5$-2-methyl-3-ethylindenyl) silanetitanium (III) 2-(N,N-dimethylamino)benzyl,
(t-butylamido)dimethyl($\eta^5$-2-methyl-3-ethylindenyl) silanetitanium (IV) dimethyl,
(t-butylamido)dimethyl($\eta^5$-2-methyl-3-ethylindenyl) silanetitanium (IV) dibenzyl,
(n-butylamido)dimethyl($\eta^5$-2-methyl-3-ethylindenyl)- silanetitanium (II) 1,4-diphenyl-1,3-butadiene,
(n-butylamido)dimethyl($\eta^5$-2-methyl-3-ethylindenyl)- silanetitanium (II) 1,3-pentadiene,
(n-butylamido)dimethyl($\eta^5$-2-methyl-3-ethylindenyl)- silanetitanium (III) 2-(N,N-dimethylamino)benzyl,
(n-butylamido)dimethyl($\eta^5$-2-methyl-3-ethylindenyl) silanetitanium (IV) dimethyl,
(n-butylamido)dimethyl($\eta^5$-2-methyl-3-ethylindenyl) silanetitanium (IV) dibenzyl, (cyclododecylamido)dimethyl($\eta^5$-2-methyl-3-ethylindenyl) silanetitanium (II) 1,4-diphenyl-1,3-butadiene,
(cyclododecylamido)dimethyl($\eta^5$-2-methyl-3-ethylindenyl) silanetitanium (II) 1,3-pentadiene,
(cyclododecylamido)dimethyl($\eta^5$-2-methyl-3-ethylindenyl) silanetitanium (III) 2-(N,N-dimethylamino)benzyl,
(cyclododecylamido)dimethyl(-2-methyl-3-ethylindenyl) silanetitanium (IV) dimethyl,
(cyclododecylamido)dimethyl($\eta^5$-2-methyl-3-ethylindenyl) silanetitanium (IV) dibenzyl,
(2,4,6-trimethylanilido)dimethyl($\eta^5$-2-methyl-3-ethyl-indenyl)silanetitanium (II) 1,4-diphenyl-1,3-1,3-butadiene,
(2,4,6-trimethylanilido)dimethyl($\eta^5$-2-methyl-3-ethylindenyl)silanetitanium (II) 1,3-pentadiene,
(2,4,6-trimethylanilido)dimethyl($\eta^5$-2-methyl-3-ethylindenyl)silanetitanium (III) 2-(N,N-dimethylamino)benzyl,
(2,4,6-trimethylanilido)dimethyl($\eta^5$-2-methyl-3-ethylindenyl)silanetitanium (IV) dimethyl,
(2,4,6-trimethylanilido)dimethyl($\eta^5$-2-methyl-3-ethylindenyl)silanetitanium (IV) dibenzyl, (1-adamantylamido)dimethyl($\eta^5$-2-methyl-3-ethylindenyl) silanetitanium (II) 1,4-diphenyl-1,3-butadiene,
(1-adamantylamido)dimethyl($\eta^5$-2-methyl-3-ethylindenyl) silanetitanium (II) 1,3-pentadiene,
(1-adamantylamido)dimethyl($\eta^5$-2-methyl-3-ethylindenyl) silanetitanium (III) 2-(N,N-dimethylamino)benzyl,
(1-adamantylamido)dimethyl($\eta^5$-2-methyl-3-ethylindenyl) silanetitanium (IV) dimethyl,
(1-adamantylamido)dimethyl($\eta^5$-2-methyl-3-ethylindenyl) silanetitanium (IV) dibenzyl, (t-butylamido)dimethyl($\eta^5$-2-methyl-3-ethylindenyl)- silanetitanium (II) 1,4-diphenyl-1,3-butadiene,
(t-butylamido)dimethyl($\eta^5$-2-methyl-3-ethylindenyl) silanetitanium (II) 1,3-pentadiene,
(t-butylamido)dimethyl($\eta^5$-2-methyl-3-ethylindenyl)- silanetitanium (III) 2-(N,N-dimethylamino)benzyl,
(t-butylamido)dimethyl($\eta^5$-2-methyl-3-ethylindenyl) silanetitanium (IV) dimethyl, (t-butylamido)dimethyl($\eta^5$-2-methyl-3-ethylindenyl)silanetitanium (IV) dibenzyl, (n-butylamido)diisopropoxy($\eta^5$-2-methyl-3-ethyl-indenyl)silanetitanium (II) 1,4-diphenyl-1,3-butadiene,
(n-butylamido)diisopropoxy($\eta^5$-2-methyl-3-ethylindenyl)silanetitanium (II) 1,3-pentadiene,
(n-butylamido)diisopropoxy($\eta^5$-2-methyl-3-ethylindenyl)silanetitanium (III) 2-(N,N-dimethylamino)benzyl,
(n-butylamido)diisopropoxy($\eta^5$-2-methyl-3-ethylindenyl)silanetitanium (IV) dimethyl,
(n-butylamido)diisopropoxy($\eta^5$-2-methyl-3-ethylindenyl)silanetitanium (IV) dibenzyl, (cyclododecylamido)diisopropoxy(-2-methyl-3-ethyl-indenyl)silanetitanium (II) 1,4-diphenyl-1,3-butadiene,
(cyclododecylamido)diisopropoxy($\eta^5$-2-methyl-3-ethylindenyl)-silanetitanium (II) 1,3-pentadiene,
(cyclododecylamido)diisopropoxy($\eta^5$-2-methyl-3-ethylindenyl)-silanetitanium (III) 2-(N,N-dimethylamino)benzyl,
(cyclododecylamido)diisopropoxy($\eta^5$-2-methyl-3-ethylindenyl)-silanetitanium (IV) dimethyl,
(cyclododecylamido)diisopropoxy($\eta^5$-2-methyl-3-ethylindenyl)-silanetitanium (IV) dibenzyl, (2,4,6-trimethylanilido)diisopropoxy($\eta^5$-2-methyl-3-ethylindenyl)silanetitanium (II) 1,4-diphenyl-1,3-butadiene,
(2,4,6-trimethylanilido)diisopropoxy($\eta^5$-2-methyl-3-ethylindenyl)silanetitanium (II) 1,3-pentadiene,
(2,4,6-trimethylanilido)diisopropoxy($\eta^5$-2-methyl-3-ethylindenyl)silanetitanium (III) 2-(N,N-dimethylamino)benzyl,
(2,4,6-trimethylanilido)diisopropoxy($\eta^5$-2-methyl-3-ethylindenyl)silanetitanium (IV) dimethyl,
(2,4,6-trimethylanilido)diisopropoxy($\eta^5$-2-methyl-3-ethylindenyl)silanetitanium (IV) dibenzyl, (1-adamantylamido)diisopropoxy($\eta^5$-2-methyl-3-ethyl-indenyl)silanetitanium (II) 1,4-diphenyl-1,3-butadiene,
(1-adamantylamido)diisopropoxy($\eta^5$-2-methyl-3-ethylindenyl)silanetitanium (II) 1,3-pentadiene,
(1-adamantylamido)diisopropoxy($\eta^5$ -2-methyl-3-ethylindenyl)silanetitanium (III) 2-(N,N-dimethylamino)benzyl,
(1-adamantylamido)diisopropoxy($\eta^5$-2-methyl-3-ethylindenyl)silanetitanium (IV) dimethyl,
(1-adamantylamido)diisopropoxy($\eta^5$-2-methyl-3-ethylindenyl)silanetitanium (IV) dibenzyl, (n-butylamido)dimethoxy($\eta^5$-2-methyl-3-ethylindenyl)silanetitanium (II) 1,4-diphenyl-1,3-butadiene,
(n-butylamido)dimethoxy($\eta^5$-2-methyl-3ethylindenyl)silanetitanium (II) 1,3-pentadiene,
(n-butylamido)dimethoxy($\eta^5$-2-methyl-3-ethylindenyl)silanetitanium (III) 2-(N,N-dimethylamino)benzyl,
(n-butylamido)dimethoxy($\eta^5$-2-methyl-3-ethylindenyl)silanetitanium (IV) dimethyl,
(n-butylamido)dimethoxy($\eta^5$-2-methyl-3-ethylindenyl)silanetitanium (IV) dibenzyl, (cyclododecylamido)dimethoxy($\eta^5$-2-methyl-3-ethyl-indenyl)silanetitanium (II) 1,4-diphenyl-1,3-butadiene,
(cyclododecylamido)dimethoxy($\eta^5$-2-methyl-3-ethylindenyl)silanetitanium (II) 1,3-pentadiene,
(cyclododecylamido)dimethoxy($\eta^5$-2-methyl-3-ethylindenyl)silanetitanium (III) 2-(N,N-dimethylamino)benzyl,
(cyclododecylamido)dimethoxy($\eta^5$-2-methyl-3-ethylindenyl)silanetitanium (IV) dimethyl,
(cyclododecylamido)dimethoxy($\eta^5$-2-methyl-3-ethylindenyl)silanetitanium (IV) dibenzyl, (2,4,6-trimethylanilido)dimethoxy($\eta^5$-2-methyl-3-ethylindenyl)silanetitanium (II) 1,4-diphenyl-1,3-butadiene,
(2,4,6-trimethylanilido)dimethoxy($\eta^5$-2-methyl-3-ethylindenyl)silanetitanium (II) 1,3-pentadiene,
(2,4,6-trimethylanilido)dimethoxy($\eta^5$-2-methyl-3-ethylindenyl)silanetitanium (III) 2-(N,N-dimethylamino)benzyl.
(2,4,6-trimethylanilido)dimethoxy($\eta^5$-2-methyl-3-ethylindenyl)silanetitanium (IV) dimethyl,
(2,4,6-trimethylanilido)dimethoxy($\eta^5$-2-methyl-3-ethylindenyl)silanetitanium (IV) dibenzyl, (1-adamantylamido)dimethoxy($\eta^5$-2-methyl-3-ethylindenyl)silanetitanium (II) 1,4-diphenyl-1,3-butadiene,
(1-adamantylamido)dimethoxy($\eta^5$-2-methyl-3-ethylindenyl)silanetitanium (II) 1,3-pentadiene,
(1-adamantylamido)dimethoxy($\eta^5$-2-methyl-3-ethylindenyl)silanetitanium (III) 2-(N,N-dimethylamino)benzyl,
(1-adamantylamido)dimethoxy($\eta^5$-2-methyl-3ethylindenyl)silanetitanium (IV) dimethyl,
(1-adamantylamido)dimethoxy($\eta^5$-2-methyl-3-ethylindenyl)silanetitanium (IV) dibenzyl, (n-butylamido)ethoxymethyl($\eta^5$-2-methyl-3-methyl-3-ethyl-indenyl)silanetitanium (II) 1,4-diphenyl-1,3-butadiene,
(n-butylamido)ethoxymethyl($\eta^5$-2-methyl-3-ethylindenyl)silanetitanium (II) 1,3-pentadiene,
(n-butylamido)ethoxymethyl($\eta^5$-2-methyl-3-ethylindenyl)silanetitanium (III) 2-(N,N-dimethylamino)benzyl,
(n-butylamido)ethoxymethyl($\eta^5$-2-methyl-3-ethylindenyl)silanetitanium (IV) dimethyl,
(n-butylamido)ethoxymethyl($\eta^5$-2-methyl-3-ethylindenyl)silanetitanium (IV) dibenzyl, (cyclododecylamido)ethoxymethyl($\eta^5$-2-methyl-3-ethyl-indenyl)silane-titanium (II) 1,4-diphenyl-1,3-butadiene,
(cyclododecylamido)ethoxymethyl($\eta^5$-2-methyl-3-ethylindenyl)silane-titanium (II) 1,3-pentadiene,
(cyclododecylamido)ethoxymethyl($\eta^5$-2-methyl-3-ethylindenyl)silane-titanium (III) 2-(N,N-dimethylamino)benzyl,
(cyclododecylamido)ethoxymethyl($\eta^5$-2-methyl-3-ethylindenyl)silanetitanium (IV) dimethyl,
(cyclododecylamido)ethoxymethyl($\eta^5$-2-methyl-3-ethylindenyl)silanetitanium (IV) dibenzyl, (2,4,6-trimethylanilido)ethoxymethyl($\eta^5$-2-methyl-3-ethylindenyl)silanetitanium (II) 1,4-diphenyl-1,3-butadiene,
(2,4,6-trimethylanilido)ethoxymethyl($\eta^5$-2-methyl-3-ethylindenyl)silanetitanium (II) 1,3-pentadiene,
(2,4.6-trimethylanilido)ethoxymethyl($\eta^5$-2-methyl-3-ethylindenyl)silanetitanium (III) 2-(N,N-dimethylamino)benzyl,
(2,4,6-trimethylanilido)ethoxymethyl($\eta^5$-2-methyl-3-ethylindenyl)silanetitanium (IV) dimethyl,
(2,4,6-trimethylanilido)ethoxymethyl($\eta^5$-2-methyl-3-ethylindenyl)silanetitanium (IV) dibenzyl, (1-adamantylamido)ethoxymethyl($\eta^5$-2-methyl-3-ethylindenyl)silanetitanium (II) 1,4-diphenyl-1,3-butadiene,
(1-adamantylamido)ethoxymethyl($\eta^5$-2-methyl-3-ethylindenyl)silanetitanium (II) 1,3-pentadiene,
(1-adamantylamido)ethoxymethyl($\eta^5$-2-methyl-3-ethylindenyl)silanetitanium (III) 2-(N,N-dimethylamino) benzyl
(1-adamantylamido)ethoxymethyl($\eta^5$-2-methyl-3-ethylindenyl)silanetitanium (IV) dimethyl,
(1-adamantylamido)ethoxymethyl($\eta^5$-2-methyl-3-ethylindenyl)silanetitanium (IV) dibenzyl, 2,3,4,6-tetramethylindenyl complexes:
(t-butylamido)dimethyl($\eta^5$-2,3,4,6-tetramethylindenyl) silanetitanium (II) 1,4-diphenyl-1,3-butadiene,
(t-butylamido)dimethyl($\eta^5$-2,3,4,6-tetramethylindenyl) silanetitanium (II) 1,3-pentadiene,
(t-butylamido)dimethyl($\eta^5$-2,3,4,6-tetramethylindenyl) silanetitanium (III) 2-(N,N-dimethylamino)benzyl,
(t-butylamido)dimethyl($\eta^5$2,3,4,6-tetramethylindenyl) silanetitanium (IV) dimethyl,
(t-butylamido)dimethyl($\eta^5$-2,3,4,6-tetramethylindenyl) silanetitanium (IV) dibenzyl, (n-butylamido)dimethyl($\eta^5$-2,3,4,6-tetramethylindenyl) silanetitanium (II) 1,4-diphenyl-1,3-butadiene,
(n-butylamido)dimethyl($\eta^5$-2,3,4,6-tetramethylindenyl) silanetitanium (II) 1,3-pentadiene,
(n-butylamido)dimethyl($\eta^5$-2,3,4,6-tetramethylindenyl)- silanetitanium (III) 2-(N,N-dimethylamino)benzyl,
(n-butylamido)dimethyl($\eta^5$-2,3,4,6-tetramethylindenyl) silanetitanium (IV) dimethyl,
(n-butylamido)dimethyl($\eta^5$-2,3,4,6-tetramethylindenyl) silanetitanium (IV)dibenzyl, (cyclododecylamido)dimethyl($\eta^5$-2,3,4,6-tetramethylindenyl)silanetitanium (II) 1,4-diphenyl-1,3-butadiene,
(cyclododecylamido)dimethyl($\eta^5$-2,3,4,6-tetramethylindenyl)silanetitanium (II) 1,3-pentadiene,
(cyclododecylamido)dimethyl($\eta^5$-2,3,4,6-tetramethylindenyl)silanetitanium (III) 2-(N,N-dimethylamino)benzyl.
(cyclododecylamido)dimethyl($\eta^5$-2,3,4,6-tetramethylindenyl)silanetitanium (IV) dimethyl,
(cyclododecylamido)dimethyl($\eta^5$-2,3,4,6-tetramethylindenyl)silanetitanium (IV) dibenzyl, (2,4,6-trimethylanilido)dimethyl($\eta^5$-2,3,4,6-tetramethylindenyl)silanetitanium (II) 1,4-diphenyl-1,3-butadiene,
(2,4,6-trimethylanilido)dimethyl($\eta^5$-2,3,4,6-tetramethylindenyl)silanetitanium (II) 1,3-pentadiene,
(2,4,6-trimethylanilido)dimethyl($\eta^5$-2,3,4,6-tetramethylindenyl)silanetitanium (III) 2-(N,N-dimethylamino) benzyl,
(2,4,6-trimethylanilido)dimethyl($\eta^5$-2,3,4,6-tetramethylindenyl)silanetitanium (IV) dimethyl,
(2,4,6-trimethylanilido)dimethyl($\eta^5$-2,3,4,6-tetramethylindenyl)silanetitanium (IV) dibenzyl, (1-adamantylamido)dimethyl($\eta^5$-2,3,4,6,-tetramethylindenyl)silanetitanium (II) 1,4-diphenyl-1,3-butadiene,
(1-adamantylamido)dimethyl($\eta^5$-2,3,4,6-tetramethylindenyl)silanetitanium (II) 1,3-pentadiene,
(1-adamantylamido)dimethyl($\eta^5$-2,3,4,6-tetramethylindenyl)silanetitanium (III) 2-(N,N-dimethylamino) benzyl,
(1-admantylamido)dimethyl($\eta^5$-2,3,4,6-tetramethylindenyl) silanetitanium (IV) dimethyl,
(1-adamantylamido)dimethyl($\eta^5$-2,3,4,6-tetramethylindenyl)silanetitanium (IV) dibenzyl,
(t-butylamido)dimethyl($\eta^5$-2,3,4,6-tetramethylindenyl)- silanetitanium (II) 1,4-diphenyl-1,3-butadiene,
(t-butylamido)dimethyl($\eta^5$-2,3,4,6-tetramethylindenyl) silanetitanium (II) 1,3-pentadiene,
(t-butylamido)dimethyl($\eta^5$-2,3,4,6-tetramethylindenyl)- silanetitanium (III) 2-(N,N-dimethylamino)benzyl,
(t-butylamido)dimethyl($\eta^5$-2,3,4,6-tetramethylindenyl) silanetitanium (IV) dimethyl,
(t-butylamido)dimethyl($\eta^5$-2,3,4,6-tetramethylindenyl) silanetitanium (IV) dibenzyl, (n-butylamido)diisopropoxy($\eta^5$-2,3,4,6-tetramethylindenyl)silane-titanium (II) 1,4-diphenyl-1,3-butadiene,
(n-butylamido)diisopropoxy($\eta^5$-2,3,4,6-tetramethylindenyl)silane-titanium (II) 1,3-pentadiene,
(n-butylamido)diisopropoxy($\eta^5$-2,3,4,6-tetramethylindenyl)-silanetitanium (III) 2-(N,N-dimethylamino)benzyl,
(n-butylamido)diisopropoxy($\eta^5$-2,3,4,6-tetramethylindenyl)silane-titanium (IV) dimethyl,
(n-butylamido)diisopropoxy($\eta^5$-2,3,4,6-tetramethylindenyl)silane-titanium (IV) dibenzyl, (cyclododecylamido)diisopropoxy($\eta^5$-2,3,4,6-tetramethylindenyl)-silanetitanium (II) 1,4-diphenyl-1,3-butadiene,
(cyclododecylamido)diisopropoxy($\eta^5$-2,3,4,6-tetramethylindenyl)silanetitanium (II) 1,3-pentadiene,
(cyclododecylamido)diisopropoxy(-2,3,4,6-tetramethylindenyl)silanetitanium (III) 2-(N,N-dimethylamino)benzyl,
(cyclododecylamido)diisopropoxy($\eta^5$-2,3,4,6-tetramethylindenyl)silanetitanium (IV) dimethyl,
(cyclododecylamido)diisopropoxy($\eta^5$-2,3,4,6-tetramethylindenyl)silanetitanium (IV) dibenzyl, (2,4,6-trimethylanilido)diisopropoxy($\eta^5$-2,3,4,6-tetramethylindenyl)silanetitanium (II) 1,4-diphenyl-1,3-butadiene,
(2,4,6-trimethylanilido)diisopropoxy($\eta^5$-2,3,4,6-tetramethylindenyl)silanetitanium (II) 1,3-pentadiene,
(2,4,6-trimethylanilido)diisopropoxy($\eta^5$-2,3,4,6-tetramethylindenyl)silanetitanium (III) 2-(N,N-dimethylamino) benzyl,
(2,4,6-trimethylanilido)diisopropoxy($\eta^5$-2,3,4,6-tetramethylindenyl)silanetitanium (IV) dimethyl,
(2,4,6-trimethylanilido)diisopropoxy($\eta^5$-2,3,4,6-tetramethylindenyl)silanetitanium (IV) dibenzyl, (1-admantylamido)diisopropoxy($\eta^5$-2,3,4,6-tetramethylindenyl)silanetitanium (III) 1,4-diphenyl-1,3-butadiene,
(1-adamantylamido)diisopropoxy($\eta^5$-2,3,4,6-tetramethylindenyl)silanetitanium (II) 1,3-pentadiene,
(1-adamantylamido)diisopropoxy($\eta^5$-2,3,4,6-tetramethylindenyl)silanetitanium (III) 2-(N,N-dimethylamino)benzyl,
(1-adamantylamido)diisopropoxy($\eta^5$-2,3,4,6-tetramethylindenyl)silanetitanium (IV) dimethyl,
(1-adamantylamido)diisopropoxy($\eta^5$-2,3,4,6-tetramethylindenyl)silanetitanium (IV) dibenzyl, (n-butylamido)dimethoxy($\eta^5$-2,3,4,6-tetramethylindenyl) silanetitanium (II) 1,4-diphenyl-1,3-butadiene,
(n-butylamido)dimethoxy($\eta^5$-2,3,4,6-tetramethylindenyl) silanetitanium (II) 1,3-pentadiene,
(n-butylamido)dimethoxy($\eta^5$-2,3,4,6-tetramethylindenyl) silanetitanium (III) 2-(N,N-dimethylamino)benzyl,
(n-butylamido)dimethoxy($\eta^5$-2,3,4,6-tetramethylindenyl) silanetitanium (IV) dimethyl,
(n-butylamido)dimethoxy($\eta^5$-2,3,4,6-tetramethylindenyl) silanetitanium (IV) dibenzyl, (cyclododecylamido)dimethoxy($\eta^5$-2,3,4,6-tetramethylindenyl)silanetitanium (II) 1,4-diphenyl-1,3-butadiene,
(cyclododecylamido)dimethoxy($\eta^5$-2,3,4,6-tetramethylindenyl)silanetitanium (II) 1,3-pentadiene,
(cyclododecylamido)dimethoxy($\eta^5$-2,3,4,6-tetramethylindenyl)silanetitanium (III) 2-(N,N-dimethylamino)benzyl,
(cyclododecylamido)dimethoxy($\eta^5$-2,3,4,6-tetramethylindenyl)silanetitanium(IV) dimethyl,
(cyclododecylamido)dimethoxy($\eta^5$-2,3,4,6-tetramethylindenyl)silanetitanium (IV) dibenzyl,
(2,4,6-trimethylanilido)dimethoxy($\eta^5$-2,3,4,6-tetramethylindenyl)silanetitanium (II) 1,4-diphenyl-1,3-butadiene,
(2,4,6-trimethylanilido)dimethoxy($\eta^5$-2,3,4,6-tetramethylindenyl)silanetitanium (II) 1,3-pentadiene,
(2,4,6-trimethylanilido)dimethoxy($\eta^5$-2,3,4,6-tetramethylindenyl)silanetitanium (III) 2-(N,N-dimethylamino) benzyl,
(2,4,6-trimethylanilido)dimethoxy($\eta^5$-2,3,4,6-tetramethylindenyl)silanetitanium (IV) dimethyl,
(2,4,6-trimethylanilido)dimethoxy($\eta^5$-2,3,4,6-tetramethylindenyl)silanetitanium (IV) dibenzyl, (1-adamantylamido)dimethoxy($\eta^5$-2,3,4,6-tetramethylindenyl)silanetitanium (II) 1,4-diphenyl-1,3-butadiene.
(1-adamantylamido)dimethoxy($\eta^5$-2,3,4,6-tetramethylindenyl)silanetitanium (II) 1,3-pentadiene,
(1-adamantylamido)dimethoxy($\eta^5$-2,3,4,6-tetramethylindenyl)silanetitanium (III) 2-(N,N-dimethylamino)benzyl,
(1-adamantylamido)dimethoxy($\eta^5$-2,3,4,6-tetramethylindenyl)silanetitanium (IV) dimethyl,
(1-adamantylamido)dimethoxy($\eta^5$-2,3,4,6-tetramethylindenyl)silanetitanium (IV) dibenzyl, (n-butylamido)ethoxymethyl($\eta^5$-2,3,4,6-tetramethylindenyl)silanetitanium (II) 1,4-diphenyl-1,3-butadiene,
(n-Butylamido)ethoxymethyl($\eta^5$-2,3,4,6-tetramethylindenyl)silanetitanium (II) 1,3-pentadiene,
(n-butylamido)ethoxymethyl($\eta^5$-2,3,4,6-tetramethylindenyl)silanetitanium (III) 2-(N,N-dimethylamino)benzyl,
(n-butylamido)ethoxymethyl($\eta^5$-2,3,4,6-tetramethylindenyl)silanetitanium (IV) dimethyl,
(n-butylamido)ethoxymethyl($\eta^5$-2,3,4,6-tetramethylindenyl)silanetitanium (IV) dibenzyl, (cyclododecylamido)ethoxymethyl($\eta^5$-2,3,4,6-tetramethylindenyl)silanetitanium (II) 1,4-diphenyl-1,3-butadiene,
(cyclododecylamido)ethoxymethyl($\eta^5$-2,3,4,6-tetramethylindenyl)silanetitanium (II) 1,3-pentadiene,
(cyclododecylamido)ethoxymethyl($\eta^5$-2,3,4,6-tetramethylindenyl)silanetitanium (III) 2-(N,N-dimethylamino)benzyl,
(cyclododecylamido)ethoxymethyl($\eta^5$-2,3,4,5-tetramethylindenyl)silanetitanium (IV) dimethyl,
(cyclododecylamido)ethoxymethyl($\eta^5$-2,3,4,6-tetramethylindenyl)silanetitanium (IV) dibenzyl, (2,4,6-trimethylanilido)ethoxymethyl($\eta^5$-2,3,4,6-tetramethylindenyl)silanetitanium (II) 1,4-diphenyl-1,3-butadiene,
(2,4,6-trimethylanilido)ethoxymethyl($\eta^5$-2,3,4,6-tetramethylindenyl)silanetitanium (II) 1,3-pentadiene,
(2,4,6-trimethylanilido)ethoxymethyl($\eta^5$-2,3,4,6-tetramethylindenyl)silanetitanium (III) 2-(N,N-dimethylamino) benzyl,
(2,4,6-trimethylanilido)ethoxymethyl($\eta^5$-2,3,4,6-tetramethylindenyl)silanetitanium (IV) dimethyl,
(2,4,6-trimethylanilido)ethoxymethyl($\eta^5$-2,3,4,6-tetramethylindenyl)silanetitanium (IV) dibenzyl, (1-adamantylamido)ethoxymethyl($\eta^5$-2,3,4,6-tetramethylindenyl)silanetitanium (II) 1,4-diphenyl-1,3-butadiene,
(1-adamantylamido)ethoxymethyl($\eta^5$-2,3,4,6-tetramethylindenyl)silanetitanium (II) 1,3-pentadiene,
(1-adamantylamido)ethoxymethyl($\eta^5$-2,3,4,6-tetramethylindenyl)silanetitanium (III) 2-(N,N-dimethylamino)benzyl,
(1-adamantylamido)ethoxymethyl($\eta^5$-2,3,4,6-tetramethylindenyl)silanetitanium (IV) dimethyl, and
(1-adamantylamido)ethoxymethyl($\eta^5$-2,3,4,6-tetramethylindenyl)silanetitanium (IV) dibenzyl.

2,3,4,6,7-pentamethylindenyl complexes:
(t-butylamido)dimethyl($\eta^5$-2,3,4,6,7-pentamethyl-indenyl) silanetitanium (II) 1,4-diphenyl-1,3-butadiene,
(t-butylamido)dimethyl($\eta^5$-2,3,4,6,7-pentamethylindenyl) silanetitanium (II) 1,3-pentadiene,
(t-butylamido)dimethyl($\eta^5$-2,3,4,6,7-pentamethylindenyl) silanetitanium (III) 2-(N,N-dimethylamino)benzyl,
(t-butylamido)dimethyl($\eta^5$2,3,4,6,7-pentamethylindenyl) silanetitanium (IV) dimethyl,
(t-butylamido)dimethyl($\eta^5$-2,3,4,6,7-pentamethylindenyl) silanetitanium (IV) dibenzyl, (n-butylamido)dimethyl($\eta^5$-2,3,4,6,7-pentamethyl-indenyl) silanetitanium (II) 1,4-diphenyl-1,3-butadiene,
(n-butylamido)dimethyl($\eta^5$-2,3,4,6,7-pentamethylindenyl) silanetitanium (II) 1,3-pentadiene,
(n-butylamido)dimethyl($\eta^5$-2,3,4,6,7-pentamethylindenyl)- silanetitanium (III) 2-(N,N-dimethylamino)benzyl,
(n-butylamido)dimethyl($\eta^5$-2,3,4,6,7-pentamethylindenyl) silanetitanium (IV) dimethyl,
(n-butylamido)dimethyl($\eta^5$-2,3,4,6,7-pentamethylindenyl) silanetitanium (IV) dibenzyl, (cyclodecylamido)dimethyl($\eta^5$-2,3,4,6,7-pentamethylindenyl)silanetitanium (II) 1,4-diphenyl-1,3-butadiene,
(cyclododecylamido)dimethyl($\eta^5$-2,3,4,6,7-pentamethylindenyl)silanetitanium (II) 1,3-pentadiene,
(cyclododecylamido)dimethyl($\eta^5$-2,3,4,6,7-pentamethylindenyl)silanetitanium (III) 2-(N,N-dimethylamino)benzyl,
(cyclododecylamido)dimethyl($\eta^5$-2,3,4,6,7-pentamethylindenyl)silanetitanium (IV) dimethyl,
(cyclododecylamido)dimethyl($\eta^5$-2,3,4,6,7-pentamethylindenyl)silanetitanium (IV) dibenzyl, (2,4,6-trimethylanilido)dimethyl($\eta^5$-2,3,4,6,7-pentamethyl-indenyl)silanetitanium (II) 1,4-diphenyl-1,3-butadiene,
(2,4,6-trimethylanilido)dimethyl($\eta^5$-2,3,4,6,7-pentamethylindenyl)silanetitanium (II) 1,3-pentadiene.
(2,4,6-trimethylanilido)dimethyl($\eta^5$-2,3,4,6,7-pentamethyl-indenyl)silanetitanium (III) 2-(N,N-dimethylamino)benzyl,
(2,4,6-trimethylanilido)dimethyl($\eta^5$-2,3,4,6,7-pentamethylindenyl)silanetitanium (IV) dimethyl,
(2,4,6-trimethylanilido)dimethyl($\eta^5$-2,3,4,6,7-pentamethylindenyl)silanetitanium (IV) dibenzyl, (1-adamantylamido)dimethyl($\eta^5$-2,3,4,6,7-pentamethylindenyl)silanetitanium (II) 1,4-diphenyl-1,3-butadiene,
(1-adamantylamido)dimethyl($\eta^5$-2,3,4,6,7-pentamethylindenyl)silanetitanium (II) 1,3-pentadiene,
(1-adamantylamido)dimethyl($\eta^5$-2,3,4,6,7-pentamethylindenyl)silanetitanium (III) 2-(N,N-dimethylamino)benzyl,
(1-adamantylamido)dimethyl($\eta^5$-2,3,4,6,7-pentamethylindenyl)silanetitanium (IV) dimethyl,
(1-adamantylamido)dimethyl)$\eta^5$-2,3,4,6,7-pentamethylindenyl)silanetitanium (IV) dibenzyl, (t-butylamido)dimethyl($\eta^5$-2,3,4,6,7-pentamethylindenyl)-silanetitanium (II) 1,4-diphenyl-1,3-butadiene,
(t-butylamido)dimethyl($\eta^5$-2,3,4,6,7-pentamethylindenyl)silanetitanium (II) 1,3-pentadiene,
(t-butylamido)dimethyl($\eta^5$-2,3,4,6,7-pentamethylindenyl)-silanetitanium (III) 2-(N,N-dimethylamino)benzyl.
(t-butylamido)dimethyl($\eta^5$-2,3,4,6,7-pentamethylindenyl) silanetitanium (IV) dimethyl,
(t-butylamido)dimethyl($\eta^5$-2,3,4,6,7-pentamethylindenyl) silanetitanium (IV) dibenzyl, (n-butylamido)diisopropoxy($\eta^5$-2,3,4,6,7-pentamethyl-indenyl)silane-titanium (II) 1,4-diphenyl-1,3-butadiene.
(n-butylamido)diisopropoxy($\eta^5$-2,3,4,6,7-pentamethylindenyl)silane-titanium (II) 1,3-pentadiene,
(n-butylamido)diisopropoxy($\eta^5$-2,3,4,6,7-pentamethylindenyl)-silanetitanium (III) 2-(N,N-dimethylamino)benzyl.
(n-butylamido)diisopropoxy($\eta^5$-2,3,4,6,7-pentamethylindenyl)silane-titanium (IV) dimethyl,
(n-butylamido)diisopropoxy($\eta^5$-2,3,4,6,7-pentamethylindenyl)silane-titanium (IV) dibenzyl, (cyclododecylamido)diisopropoxy($\eta^5$-2,3,4,6,7-pentamethyl-indenyl)-silanetitanium (II) 1,4-diphenyl-1,3,-butadiene.
(cyclododecylamido)diisopropoxy($\eta^5$-2,3,4,6,7-pentamethylindenyl)silanetitanium (II) 1,3-pentadiene,
(cyclododecylamido)diisopropoxy(-2,3,4,6,7-pentamethylindenyl)silanetitanium (III) 2-(N,N-dimethylamino)benzyl,
(cyclododecylamido)diisopropoxy($\eta^5$-2,3,4,6,7-pentamethylindenyl)silanetitanium (IV) dimethyl,
(cyclododecylamido)diisopropoxy($\eta^5$-2,3,4,6,7-pentamethylindenyl)silanetitanium (IV) dibenzyl,
(2,4,6-trimethylanilido)diisopropoxy($\eta^5$-2,3,4,6,7-pentamethylindenyl)silanetitanium (II) 1,4-diphenyl-3,4-butadiene,
(2,4,6-trimethylanilido)diisopropoxy($\eta^5$-2,3,4,6,7-pentamethylindenyl)silanetitanium (II) 1,3-pentadiene,
(2,4,6-trimethylanilido)diisopropoxy($\eta^5$-2,3,4,6,7-pentamethylindenyl)silanetitanium (III) 2-(N,N-dimethylamino) benzyl,
(2,4,6-trimethylanilido)diisopropoxy($\eta^5$-2,3,4,6,7-pentamethylindenyl)silanetitanium (IV) dimethyl,
(2,4,6-trimethylanilido)diisopropoxy($\eta^5$-2,3,4,6,7-pentamethylindenyl)silanetitanium (IV) dibenzyl, (1-adamantylamido)diisopropoxy($\eta^5$-2,3,4,6,7-pentamethyl-indenyl)silanetitanium (II) 1,4-diphenyl-1,3-butadiene,
(1-adamantylamido)diisopropoxy($\eta^5$-2,3,4,6,7-pentamethylindenyl)silanetitanium (II) 1,3-pentadiene,
(1-adamantylamido)diisopropoxy($\eta^5$-2,3,4,6,7-pentamethylindenyl)silanetitanium (III) 2-(N,N-dimethylamino) benzyl,
(1-adamantylamido)diisopropoxy($\eta^5$-2,3,4,6,7-pentamethylindenyl)silanetitanium (IV) dimethyl,
(1-adamantylamido)diisopropoxy($\eta^5$-2,3,4,6,7-pentamethylindenyl)silanetitanium (IV) dibenzyl, (n-butylamido)dimethoxy($\eta^5$-2,3,4,6,7-pentamethylindenyl)silanetitanium (II) 1,4-diphenyl-1,3-butadiene,
(n-butylamido)dimethoxy($\eta^5$-2,3,4,6,7-pentamethylindenyl)silanetitanium (II) 1,3-pentadiene,
(n-butylamido)dimethoxy($\eta^5$-2,3,4,6,7-pentamethylindenyl)silanetitanium (III) 2-(N,N-dimethylamino)benzyl,
(n-butylamido)dimethoxy($\eta^5$-2,3,4,6,7-pentamethylindenyl)silanetitanium (IV) dimethyl,
(n-butylamido)dimethoxy($\eta^5$-2,3,4,6,7-pentamethylindenyl)silanetitanium (IV) dibenzyl, (cyclododecylamido)dimethoxy($\eta^5$-2,3,4,6,7-pentamethylindenyl)silanetitanium (II) 1,4-diphenyl-1,3-butadiene,
(cyclododecylamido)dimethoxy($\eta^5$-2,3,4,6,7-pentamethylindenyl)silanetitanium (II) 1,3-pentadiene,
(cyclododecylamido)dimethoxy($\eta^5$-2,3,4,6,7-pentamethylindenyl)silanetitanium (III) 2-(N,N-dimethylamino)benzyl,
(cyclododecylamino)dimethoxy($\eta^5$-2,3,4,6,7-pentamethyl)silanetitanium (IV) dimethyl,
(cyclododecylamido)dimethoxy($\eta^5$-2,3,4,6,7-pentamethylindenyl)silanetitanium (IV) dibenzyl, (2,4,6-trimethylanilido)dimethoxy($\eta^5$-2,3,4,6,7-pentamethylindenyl)silanetitanium (II) 1,4-diphenyl-1,3-butadiene,
(2,4,6-trimethylanilido))dimethoxy($\eta^5$-2,3,4,6,7-pentamethylindenyl)silanetitanium (II) 1,3-pentadiene,
(2,4,6-trimethylanilido)dimethoxy($\eta^5$-2,3,4,6,7-pentamethylindenyl)silanetitanium (III) 2-(N,N-dimethylamino) benzyl,
(2,4,6-trimethylanilido)dimethoxy($\eta^5$-2,3,4,6,7-pentamethylindenyl)silanetitanium (IV) dimethyl,
(2,4,6-trimethylanilido)dimethoxy($\eta^5$-2,3,4,6,7-pentamethylindenyl)silanetitanium (IV) dibenzyl, (1-adamantylamido)dimethoxy($\eta^5$-2,3,4,6,7-pentamethylindenyl)silanetitanium (II) 1,4-diphenyl-1,3-butadiene,
(1-adamantylamido)dimethoxy($\eta^5$-2,3,4,6,7-pentamethylindenyl)silanetitanium (II) 1,3-pentadiene,
(1-adamantylamido)dimethoxy($\eta^5$-2,3,4,6,7-pentamethylindenyl)silanetitanium (III) 2-(N,N-dimethylamino) benzyl,
(1-adamantylamido)dimethoxy($\eta^5$-2,3,4,6,7-pentamethylindenyl)silanetitanium (IV) dimethyl, (1-adamantylamido)dimethoxy($\eta^5$-2,3,4,6,7-pentamethylindenyl)silanetitanium (IV) dibenzyl, (n-butylamido)ethoxymethyl($\eta^5$-2,3,4,6,7-pentamethylindenyl)silanetanium (II) 1,4-diphenyl-1,3-butadiene,
(n-butylamido)ethoxymethyl($\eta^5$-2,3,4,6,7-pentamethylindenyl)silanetitanium (II) 1,3-pentadiene,
(n-butylamido)ethoxymethyl($\eta^5$-2,3,4,6,7-pentamethylindenyl)silanetitanium (III) 2-(N,N-dimethylamino) benzyl,
(n-butylamido)ethoxymethyl($\eta^5$-2,3,4,6,7-pentamethylindenyl)silanetitanium (IV) dimethyl,
(n-butylamido)ethoxymethyl($\eta^5$-2,3,4,6,7-pentamethylindenyl)silanetitanium (IV) dibenzyl,
(cyclododecylamido)ethoxymethyl($\eta^5$-2,3,4,6,7-pentamethylindenyl)silanetitanium (II) 1,4-diphenyl-1,3-butadiene,
(cyclododecylamido)ethoxymethyl($\eta^5$-2,3,4,6,7-pentamethylindenyl)silanetitanium (II) 1,3-pentadiene,
(cyclododecylamido)ethoxymethyl($\eta^5$-2,3,4,6,7-pentamethylindenyl)silanetitanium (III) 2-(N,N-dimethylamino)benzyl,
(cyclododecylamido)ethoxymethyl($\eta^5$-2,3,4,6,7-pentamethylindenyl)silanetitanium (IV) dimethyl,
(cyclododecylamido)ethoxymethyl($\eta^5$-2,3,4,6,7-pentamethylindenyl)silanetitanium (IV) dibenzyl, (2,4,6-trimethylanilido)ethoxymethyl($\eta^5$-2,3,4,6,7-pentamethylindenyl)silanetitanium (II) 1,4-diphenyl-1,3-butadiene,
(2,4,6-trimethylanilido)ethoxymethyl($\eta^5$-2,3,4,6,7-pentamethylindenyl)silanetitanium (II) 1,3-pentadiene,
(2,4,6-trimethylanilido)ethoxymethyl($\eta^5$-2,3,4,6,7-pentamethylindenyl)silanetitanium (III) 2-(N,N-dimethylamino) benzyl,
(2,4,6-trimethylanilido)ethoxymethyl($\eta^5$-2,3,4,6,7-pentamethylindenyl)silanetitanium (IV)dimethyl,
(2,4,6-trimethylanilido)ethoxymethyl($\eta^5$-2,3,4,6,7-pentamethylindenyl)silanetitanium (IV) dibenzyl, (1-adamantylamido)ethoxymethyl($\eta^5$-2,3,4,6,7-pentamethyl-indenyl)silanetitanium (II) 1,4-diphenyl-1,3-butadiene,
(1adamantylamido)ethoxymethyl($\eta^5$-2,3,4,6,7-pentamethylindenyl)silanetitanium (II) 1,3-pentadiene,
(1-adamantylamido)ethoxymethyl($\eta^5$-2,3,4,6,7-pentamethylindenyl)silanetitanium (III) 2-(N,N-dimethylamino) benzyl,
(1-adamantylamido)ethoxymethyl($\eta^5$-2,3,4,6,7-pentamethylindenyl)silanetitanium (IV) dimethyl, and
(1-adamantylamido)ethoxymethyl($\eta^5$-2,3,4,6,7-pentamethylindenyl)silanetitanium (IV) dibenzyl, The complexes can be prepared by use of well known synthetic techniques. Optionally a reducing agent can be employed to produce the tower oxidation state complexes. Such a process is disclosed in U.S. Ser. No. 8/241,523, filed May 13, 1994, published as WO95-00526. The reactions are conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene $C_{1-4}$ dialkyl ethers $C_{1-4}$ dialkyl ether derivatives of (poly)alkylene glycols, and tetrahydrofuran. Mixtures of the foregoing are also suitable.

The complexes are rendered catalytically active by combination with an activating cocatalyst or by use of an activating technique. Suitable activating cocatalysts for use here in include polymeric or oligomeric alumoxanes, especially methylalumoxane, triisobutyl aluminum modified methylalumoxane, isobutyalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,5064,802, EP-A-468,651 (equivalent to U.S. Ser. No. 07/547,718), EP-A-520,732 (equivalent to U.S. Ser. No. 07/876,268), and EP-A-520,732 (equivalent to U.S. Ser. Nos. 07/884,966 filed May 1, 1992).

Combinations of neutral Lewis acids, especially the combination of a trialkyl aluminum compound having from 1 to 4 carbons in each alkyl groups and a halogenated tri (hydrocarbyl)boron compound having from 1 to 20 carbons in each alkyl hydrocarbyl group, especially tris (pentafluorophenyl)borane, further combinations of such neutral Lewis acid mixtures with a polymeric or oligomeric alumnoxane, and combinations of a single neutral Lewis acid, especially tris(pentafluorophenyl)borane with a polymeric or oligomeric alumoxane are especially desirable activating cocatalysts. A benefit according to the present invention is the discovery that the most efficient catalyst activation using such a combination of tris (pentafluorophenol)borane/alumoxane mixture occurs at reduced levels of alumoxane. Preferred molar ratios of Group 4 metal complex:tris(pentafluorophenylborane:alumoxane are from 1:1:1 to 1:5:5, more preferably from 1:1:1.5 to 1:5:3. The surprising efficient use of lower levels of alumoxane with the present invention allows for the production of olefin polymers with high catalytic efficiencies using less of the expensive alumoxane cocatalyst. Additionally, polymers with lower levels of aluminum residue, and hence greater clarity, are obtained.

Suitable ion forming compounds useful as cocatalysts in one embodiment of the present invention comprise a cation which is a Bronsted acid capable of donating a proton, and a compatible, noncoordinating anion, A⁻, As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula: $(L^*—H)_d^+(A)^{d-}$
wherein:
$L^*$ is a neutral Lewis base;
$(L^*—H)+$ is a Bronsted acid;
$A_{d-}$ is a noncoordinating, compatible anion having a charge of d−, and
d is an integer from 1 to 3.

More preferably $A^{d-}$ corresponds to the formula:$[M'Q_4]^-$;
wherein:
M' is boron or aluminum in the +3 formal oxidation state; and
Q independently each occurrence is selected from hydride, dialkylamido, halide, hydrocarbyl, hydrocarbyloxide, halosubstituted-hydrocarbyl, halosubstituted hydrocarbyloxy, and halo- substituted silylhydrocarbyl radicals (including perhalogenated hydrocarbyl- perhalogenated hydrocarbyloxy- and perhalogenated silyhydrocarbyl radicals), said Q having up to 20 carbons with the proviso that in not more than one occurrence is Q halid. Examples of suitable hydrocarbyloxide Q groups are disclosed in U.S. Pat. No. 5,296,433.

In a more preferred embodiment, d is one, that is, the counter ion has a single negative charge and is A⁻. Activating cocatalysts comprising boron which are particularly useful in the preparation of catalysts of this invention may be represented by the following general formula: $(L^*—H)^+ (BQ_4)$:
wherein:
$L^*$ is as previously defined;
B is boron in a formal oxidation state of 3; and
Q is a hydrocarbyl, hydrocarbyloxy-, fluorinated hydrocarbyl-, fluorinated hydrocarbyloxy-, or fluorinated silylhydrocarbyl- group of up to 20 nonhydrogen atoms, with the proviso that in not more than one occasion is Q hydrocarbyl.

Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl) borate,
tri(sec-butyl)ammonium tetrakis(pentafluoropheny) borate,
N,N-dimethylanilinium tetrakis(pentafluorophenyl)borate,
N,N-dimethylanilinium n-butyltris(pentafluorophenyl) borate,
N,N-dimethylanilinium benzyltris(pentafluorophenyl) borate,
N,N-dimethylanilinium tetrakis(4-(t-butyldimethylsilyl)-2,3,5,6-tetrafluorphenyl) borate,
N,N-dimethylanilinium tetrakis(4-triisopropylsilyl)-2,3,5,6-tetrafluorophenyl) borate,
N,N-dimethylanilinium pentafluorophenoxytris (pentafluorophenyl) borate,
N,N-diethylanilinium tetrakis(pentafluorophenyl) borate,
N,N-dimethyl-2,4,6-trimethylanilinium tetrakis (pentafluorophenyl) borate,
trimethylammonium tetrakis(2,3,4,6-tetrafluorophenyl) borate,
triethylammonium tetrakis(2,3,4,6-tetrafluorophenyl) borate,
tripropylammonium tetrakis(2,3,4,6-tetrafluorophenyl) borate,
tri(n-butyl)ammonium tetrakis(2,3,4,6-tetrafluorophenyl) borate,
dimethyl(t-butyl)ammonium tetrakis(2,3,4,6-tetrafluorophenyl) borate,
N,N-dimethylanilinium tetrakis(2,3,4,6-tetrafluorophenyl) borate,
N,N-diethylanilinium tetrakis(2,3,4,6-tetrafluorophenyl) borate, and
N,N-dimethyl-2,4,6-trimethylanilinium tetrakis(2,3,4,6-tetrafluorophenyl) borate;

dialkyl ammonium salts such as:
di-(i-propyl)ammonium tetrakis(pentafluorophenyl) borate, and
dicyclohexylammonium tetrakis(pentafluorophenyl) borate;
tri-substituted phosphonium salts such as:
triphenylphosphonium tetrakis(pentafluorophenyl) borate,
tri(o-tolyl)phosphonium tetrakis(pentafluorophenyl) borate, and
tri(2,6-dimethylphenyl)phosphonium tetrakis (pentafluorophenyl) borate;
di-substituted oxonium salts such as:
diphenyloxonium tetrakis(pentafluorophenyl) borate,
di(o-tolyl)oxonium tetrakis(pentafluorophenyl) borate, and
di(2,6-dimethylphenyl)oxonium tetrakis(pentafluorophenyl) borate;
di-substituted sulfonium salts such as:
diphenylsulfonium tetrakis(pentafluorophenyl) borate,
di(o-tolyl)sulfonium tetrakis(pentafluorophenyl) borate, and
bis(2,6-dimethylphenyl)sulfonium tetrakis (pentafluorophenyl) borate.

Preferred $(L^*—H)^+$ cations are N,N-dimethylanilinium and tributylammonium.

Another suitable ion forming, activating cocatalyst comprises a salt of a cationic oxidizing agent and a noncoordinating, compatible anion represented by the formula:

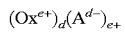

$(Ox^{e+})_d(A^{d-})_{e+}$ wherein:

$Ox^{e+}$ is a cationic oxidizing agent having a charge of e+;

e is an integer from 1 to 3; and $A^{d-}$ and d are as previously defined.

Examples of cationic oxidizing agents include: ferrocenium, hydrocarbyl-substituted ferrocenium, $Ag^-$ or $Pb^{+2}$. Preferred embodiments of $A^{d-}$ are those anions previously defined with respect to the bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$\copyright^+ A^-$ wherein:

$\copyright^+$ is a $C_{1-20}$ carbenium ion; and $A^-$ is as previously defined. A preferred carbenium ion is the trityl cation, that is triphenylmethylium.

A further suitable ion forming, activating cocatalyst comprises a compound which is a salt of a silylium ion and a noncoordinating, compatible anion represented by the formula:

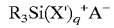

$R_3Si(X')_q{}^+ A^-$ wherein:

R is $C_{1-10}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in J. Chem Soc. Chem. Comm., 1993, 383–384, as well as Lambert, J. B., et at., Organometallics, 1994, 13, 2430–2443. The use of the above silylium salts as activating cocatalysts for addition polymerization catalysts is claimed in United States Patent Application entitled. Silylium Cationic Polymerization Activators For Metallocene Complexes, filed in the names of David Neithamer, David Devore, Robert LaPointe and Robert Mussell on Sep. 12, 1994.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, A–. Preferred supporting electrolytes are salts corresponding to the formula $G^+A^-$: wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra(n-butylammonium)- and tetraethylammonium- cations.

During activation of the complexes of the present invention by bulk electrolysis the cation of the supporting electrolyte passes to the counter electrode and A– migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl)borates having from 1 to 10 carbons in each hydrocarbyl or perfluoroaryl group, especially tetra(n-butylammonium)tetrakis(pentafluorophenyl)borate.

A further recently discovered electrochemical technique for generation of activating cocatalysts is the electrolysis of a disilane compound in the presence of a source of a noncoordinating compatible anion. This technique is more fully disclosed and claimed in the previously mentioned United States Patent application entitled, "Silylium Cationic Polymerization Activators For Metallocene Complexes", filed on Sep. 12, 1994.

The foregoing electrochemical activating technique and activating cocatalysts may also be used in combination. An especially preferred combination is a mixture of a tri (hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumonxane, when used by itself as an activating cocatalyst, is employed in large quantity, generally at least 100 times the quantity of metal complex on a molar basis. Tris (pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The process may be used to polymerize ethylenically unsaturated monomers having from 3 to 20 carbon atoms either alone or in combination. Preferred monomers include monovinylidene aromatic monomers, 4-vinylcyclohexene, vinylcyclohexane, norbornadiene and $C_{3-10}$ aliphatic α-olefins (especially ethylene, propylene, isobutylene, 1-butene, 1-hexene, 3-methyl-1-pentene, 4-methyl-1-pentene, and 1-octene), $C_{4-40}$ dienes, and mixtures thereof. Most preferred monomers are ethylene, and mixtures of ethylene, propylene and a nonconjugated diene, especially ethylidenenorbornene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents for polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and the like and aromatic and alkyl-substituted aromatic compounds such as benzene, toluene, xylene, ethylbenzene and the like. Suitable solvents also include liquid olefins which may act as monomers or comonomers including ethylene, propylene, butadiene, cyclopentene, 1-hexene, 1-hexane, 4-vinylcyclohexene, vinylcyclohexane, 3-methyl-1-pentene, 4-methyl-1-pentene, 1,4-hexadiene, 1-octone, 1-decene, styrene, divinylbenzene, allylbenzene, vinyltoluene (including all isomers alone or in admixture), and the like. Mixtures of the foregoing are also suitable.

The catalysts may be utilized in combination with at least one additional homogeneous or heterogeneous polymerization in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993.

Utilizing the catalysts of the present invention copolymers having high comonomer incorporation and correspondingly low density, yet having a low melt index may be readily prepared. That is, high molecular weight polymers are readily attained by use of the present catalysts even at elevated reactor temperatures. This result is highly desirable because the molecular weight of α-olefin copolymers can be readily reduced by the use of hydrogen or similar chain transfer agent, however increasing the molecular weight of α-olefin copolymers is usually only attainable by reducing the polymerization temperature of the reactor. Disadvantageously, operation of a polymerization reactor at reduced temperatures significantly increases the cost of operation since heat must be removed from the reactor to maintain the reduced reaction temperature, while at the same time heat must be added to the reactor effluent to vaporize the solvent. In addition, productivity is increased due to improved polymer solubility, decreased solution viscosity, and a higher polymer concentration. Utilizing the present catalysts. α-olefin homopolymers and copolymers having densities from 0.85 g/cm³ to 0.96 g/cm³, and melt flow rates from 0.001 to 10.0 dg/min are readily attained in a high temperature process.

The catalysts of the present invention are particularly advantageous for the production of ethylene homopolymers and ethylene/α-olefin copolymers having high levels of long chain branching. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalysts system advantageously allows for the economical production of ethylene/α-olefin copolymers having processability similar to high pressure, free radical produced low density polyethylene.

The present catalysts system may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a C3–20 α-olefin and a "H"-branching comonomer. Preferably, such polymers are produced in a solution process, most preferably a continuous solution process.

As previously mentioned, the present catalyst system is particularly useful in the preparation of EP and EPDM copolymers in high yield and productivity. The process employed may be either a solution or slurry process both of which are previously known in the art. Kaminsky, *J. Poly. Sci.*, Vol. 23, pp. 2151–64 (1985(reported the use of a soluble bis(cyclopentadienyl)zirconium dimethyl-alumoxane catalyst system for solution polymerization of EP and EPDM elastomers. U.S. Pat. No. 5,229,478 disclosed a slurry polymerization process utilizing similar bis (cyclopentadienyl)zirconium based catalyst systems.

In general terms, it is desirable to produce such EP and EPDM elastomers under conditions of increased reactivity of the diene monomer component. The reason for this was explained in the above identified '478 patent in the following manner, which still remains true despite the advances attained in such reference. A major factor affecting production costs and hence the utility of an EPDM is the diene monomer cost. The diene is a more expensive monomer material than ethylene or propylene. Further, the reactivity of diene monomers with previously known metallocene catalysts is lower than that of ethylene and propylene. Consequently, to achieve the requisite degree of diene incorporation to produce an EPDM with an acceptably fast cure rate, it has been necessary to use a diene monomer concentration which, expressed as a percentage of the total concentration of monomers present, is in substantial excess compared to the percentage of diene desired to be incorporated into the final EPDM product. Since substantial amounts of unreacted diene monomer must be recovered from the polymerization reactor effluent for recycle the cost of production is increased unnecessarily.

Further adding to the cost of producing an EPDM is the fact that, generally, the exposure of an olefin polymerization catalyst to a diene, especially the high concentrations of diene monomer required to produce the requisite level of diene incorporation in the final EPDM product, often reduces the rate or activity at which the catalyst will cause polymerization of ethylene and propylene monomers to proceed. Correspondingly, lower throughputs and longer reaction times have been required, compared to the production of an ethylene-propylene copolymer elastomer or other $\alpha$-olefin copolymer elastomer.

The present catalyst system advantageously allows for increased diene reactivity thereby preparing EPDM polymers in high yield and productivity. Additionally, the catalyst system of the present invention achieves the economical production of EPDM polymers with diene contents of up to 20 weight percent or higher, which polymers possess highly desirable fast cure rates.

The non-conjugated diene monomer can be a straight chain, branched chain or cyclic hydrocarbon diene having from 6 to 15 carbon atoms. Examples of suitable non-conjugated dienes are straight chain acyclic dienes such as 1,4-hexadiene and 1,6-octadiene; branched chain acyclic dienes such as 5-methyl-1,4-hexadiene; 3,7-dimethyl-1,6-octadiene; 3,7-dimethyl-1,7-octadiene and mixed isomers of dihydromyricene and dihydroocinene; single ring alicyclic dienes such as 1,3-cyclopentadiene; 1,4-cyclohexadiene; 1,5-cyclooctadiene and 1,5-cyclododecadiene; and multi-ring alicyclic fused and bridged ring dienes such as tetrahydroindene, methyl tetrahydroindene, dicyclopentadiene; bicyclo-(2,2,1)-hepta-2,5-diene; alkenyl, alkylidene, cycloalkenyl and cycloalklidene norbornenes such as 5-methylene-2-norbornene (MNB); 5-propenyl-2-norbornene, 5-isopropylidene-2-norbornene,5-(4-cyclopentenyl)-2-norbornene,5-cyclohexylidene-2-norbornene, 5-vinyl-2-norbornene and norbornadiene.

Of the dienes typically used to prepare EPDMs, the particularly preferred dienes are 1,4-hexadiene (HD), 5-ethylidene-2-norbornene (ENB), 5-vinylidene-2-norbornene (VNB), 5-methylene-2-norbornene (MNB), and dicyclopentadiene (DCPD). The especially preferred dienes are 5-ethylidene-2-norbornene (ENB) and 1,4-hexadiene (HD).

The preferred EPDM elastomers may contain 20 up to 90 weight percent ethylene, more preferably 30 to 85 weight percent ethylene, most preferably 35 to 80 weight percent ethylene.

The alpha-olefins suitable for use in the preparation of elastomers with ethylene and dienes are preferably $C_{3-16}$ alpha-olefins, illustrative non-limiting examples of such alpha-olefins are propylene, 1-butene, 1-pentene, 1-hexene, 1-octene, 1-decene, and 1-dodecene. The alpha-olefin is generally incorporated into the EPDM polymer at 10 to 80 weight percent, more preferably at 20 to 65 weight percent. The non-conjugated dienes are generally incorporated into the EPDM at 0.5 to 20 weight percent; more, preferably at 1 to 15 weight percent, and most preferably at 3 to 12 weight percent. If desired, more than one diene may be incorporated simultaneously, for example HD and ENB, with total diene incorporation within the limits specified above.

The catalyst system may be prepared as a homogeneous catalyst by addition of the requisite components to a solvent in which polymerization will be carried out by solution polymerization procedures. The catalyst system may also be prepared and employed as a heterogeneous catalyst by adsorbing the requisite components on a catalyst support material such as silica gel, alumina or other suitable inorganic support material. When prepared in heterogeneous or supported form, it is preferred to use silica as the support material. The heterogeneous form of the catalyst system is employed in a slurry polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the $\alpha$-olefin monomer or a mixture of different $\alpha$-olefin monomers may be used in whole or part as the diluent. Most preferably the diluent comprises in at least major part the $\alpha$-olefin monomer or monomers to be polymerized.

In contrast, solution polymerization conditions utilize a solvent for the respective components of the reaction, particularly the EP or EPDM polymer. Preferred solvents include mineral oils and the various hydrocarbons which are liquid at reaction temperatures. Illustrative examples of useful solvents include alkanes such as pentane, iso-pentane, hexane, heptane, octane and nonane, as well as mixtures of alkanes including kerosene and Isopar E™, available from Exxon Chemicals Inc.; cycloalkanes such as cyclopentane and cyclohexane; and aromatics such as benzene, toluene, xylenes, ethylbenzene and diethylbenzene.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas such as, for example, nitrogen.

Ethylene is added to the reaction vessel in an amount to maintain a differential pressure in excess of the combined vapor pressure of the $\alpha$-olefin and diene monomers. The ethylene content of the polymer is determined by the ratio of ethylene differential pressure to the total reactor pressure. Generally the polymerization process is carried out with a differential pressure of ethylene of from 10 to 1000 psi (70 to 7000 kPa), most preferably from 40 to 400 psi (30 to 300 kPa). The polymerization is generally conducted at a temperature of from 25 to 200° C., preferably from 75 to 170° C., and most preferably from greater than 95 to 140° C.

The polymerization may be carried out as a batchwise or a continuous polymerization process A continuous process is preferred, in which event catalyst, ethylene, $\alpha$-olefin, and optionally solvent and diene are continuously supplied to the reaction zone and polymer product continuously removed therefrom.

Without limiting in any way the scope of the invention, one means for carrying out such a polymerization process is as follows: In a stirred-tank reactor propylene monomer is introduced continuously together with solvent, diene monomer and ethylene monomer. The reactor contains a liquid phase composed substantially of ethylene, propylene and diene monomers together with any solvent or additional diluent. If desired, a small amount of a "H"-branch inducing diene such as norbornadiene, 1,7-octadiene or 1,9=-decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to propylene in the reactor, which is controlled by manipulating the respective feed rates of these components to the reactor. The polymer product molecular weight is controlled, optionally, by controlling other polymerization variables such as the temperature, monomer concentration, or by a stream of hydrogen introduced to the reactor, as is well known in the art. The reactor effluent is contacted with a catalyst kill agent such as water. The polymer solution is optionally heated, and the polymer product is recovered by flashing off gaseous ethylene and propylene as well as residual solvent or diluent at reduced pressure, and, if necessary, conducting further devolatilization in equipment such as a devolatilizing extruder. In a continuous process the mean residence time of the catalyst and polymer in the reactor generally is from 5 minutes to 8 hours, and preferably from 10 minutes to 6 hours.

In a preferred manner of operation, the polymerization is conducted in a continuous solution polymerization system comprising two reactors connected in series or parallel. In one reactor a relatively high molecular weight product (Mw from 300,000 to 600,000, more preferably 400,000 to 500,000) is formed while in the second reactor a product of a relatively low molecular weight (Mw 50,000 to 300,000) is formed. The final product is a blend of the two reactor effluents which are combined prior to devolatilization to result in a uniform blend of the two polymer products. Such a dual reactor process allows for the preparation of products having improved properties. In a preferred embodiment the reactors are connected in series, that is effluent from the first reactor is charged to the second reactor and fresh monomer, solvent and hydrogen is added to the second reactor. Reactor conditions are adjusted such that the weight ratio of polymer produced in the first reactor to that produced in the second reactor is from 20:80 to 80:20. In addition the temperature of the second reactor is controlled to produce the lower molecular weight product. This system beneficially allow for production of EPDM products having a large range of Mooney viscosities, as well as excellent strength and processability. Preferably the Mooney viscosity (ASTM D1646-94, ML1+4@125° C.) of the resulting product is adjusted to fall in the range from 1 to 200, preferably from 5 to 150 m and most preferably from 10 to 110.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis.

$^1$H and $^{13}$C NMR spectra were recorded on a Varian XL (300 MHz) spectrometer. Chemical shifts were determined relative to TMS or through the residual $CHCl_3$ in $CDCl_3$ or the residual $C_6HD_5$ in $C_6D_6$, relative to TMS. Tetrahydrofuran (THF), diethylether, toluene, and hexane were used following passage through double columns charged with activated alumina and alumina supported mixed metal oxide catalyst (Q-5® catalyst, available from Engelhard Corp.) The compounds n-BuLi, KH, all Grignard reagents, and 1,4-diphenyl-1,3-butadiene were all used as purchased from Aldrich Chemical Company. All syntheses were performed under dry nitrogen atmosphere using a combination of glove box and high vacuum techniques.

Example 1

Preparation of (2-methylindenyl)dimethyl(t-butylamido)silanetitanium dichloride

Preparation of 2-Bromoindene

To a 500 mL flask containing a magnetic stir bar was added (+/-)trans-2-bromo-1-indanol (50.0 g, 235 mmol), p-toluenesulfonic acid monohydrate (0.50 g, 2.6 mmol), and toluene (300 mL). A Dean Stark trap and reflux condenser were placed on the flask, and the reaction was refluxed for 16 hours. The reaction was transferred to a separatory funnel, chloroform was added (200 mL), and the resulting mixture was washed with aqueous sodium bicarbonate solution (3×200 mL). The organic layer was then washed with a saturated aqueous sodium chloride solution (1×300 mL), dried over anhydrous magnesium sulfate, and filtered. The solvents were removed and distillation provided 40.6 g (88.7 percent) of the slightly yellow crystalline solid collected at 72–105° C. at 3 mm Hg.

$^1$H NMR (300 MHz, $CDCl_3$, TMS); δ7.4–7.1(m, 4H), 6.93(s, 1H), 3.60(s, 2H).

$^{13}$C NMR (75 MHz, $CDCl_3$): δ143.62, 142.22, 132.64, 126.38, 124.59, 124.49, 122.85, 119.88, 45.40.

GC-MS: Calculated for $C_9H_7$ $^{79}Br$ 193.97, found 194.00. Calculated for $C_9H_7$ $^{81}Br$ 195.90, found 195.90.

Preparation of 2-Methylindene via 2-Bromoindene

2-Bromoindene (24.4 g, 0.125 moles) and Ni(dppp)$Cl_2$ (0.925 g, 1.71×10$^{-3}$ moles) (dppp=1,3-bis(diphenylphosphino)propane) were stirred in diethylether (200 mL) at −78° C. under a nitrogen atmosphere as methylMgBr (0.150 moles, 50.00 mL of 3.0 M solution in diethylether) was added. The dry-ice bath was then immediately removed and the reaction mixture allowed to warm to room temperature. The reaction mixture started off as a heterogeneous brick-red color and then turned to a homogeneous yellow/gold solution. After an hour of stirring in this state an exotherm occurred which resulted in some refluxing of the ether in the flask. The solution then turned back to the heterogeneous brick-red mixture. Total stirring time for the mixture was 3 hours following the removal of the ice-bath after which time GC analysis showed that the conversion of 2-bromoindene to 2-methylindene was substantially quantitative. After the reaction period the mixture was poured onto ice and then extracted with 1 M HCL (1×100 mL) and 1 M $NaHCO_3$ (1×100 mL) and then dried with $MgSO_4$ and filtered. The desired product was isolated as a light yellow oil (14.0 g, 86.2 percent).

$^1$H NMR (300 MHz, $CDCl_3$); δ2.18 (s, 3H), 3.32 (s, 2H), 6.51 (s, 1H), 7.08–7.40 (m, 4H).

$^{13}$C NMR (75 MHZ, $CDCl_3$); δ17.02, 42.90, 119.71, 123.30, 123.49, 126.22, 127.16, 143.30, 145.90, 146.04.

GC-MS: Calculated for $C_{10}H_{10}$ 130.19, found 130.00.

Preparation of 2-Methylindene via 2-Methylindanone

2-Methylindanone (20.0 g, 0.137 moles) and $NaBH_4$ (5.175 g, 0.137 moles) were mixed together and stirred in THF (200 mL). Anhydrous ethanol (100 mL) was then slowly added and the mixture allowed to stir for 16 hours at room temperature. After the reaction period the mixture was quenched by the slow addition of 1 M HCl and then extracted using diethylether (3×100 mL). Removal of the solvent resulted in the isolation of a white solid which was then redissolved in diethylether (300 mL) and stirred over cationic ion exchange beads (Dowex™ DR-2030 ion exchange beads, available from The Dow Chemical Company) for 48 hours while monitoring the reaction using a gas chromatograph. The mixture was then filtered and the volatiles removed resulting in the isolation of the desired product as a pale yellow oil (16.8 g, 94.3 percent).

Preparation of Lithium-2-Methylindenide

2-Methylindene (15.5 g, 0.114 moles) was stirred in diethylether (250 mL) as n-BuLi (0.120 moles, 60.0 mL of 2.0 M solution in cyclohexane) was added dropwise. The mixture was then allowed to stir for 3 hours at room temperature. After the reaction period the volatiles were removed and the solid washed well with hexane and collected via suction filtration as a light yellow powder which was used without further purification or analysis (15.1 g, 97.0 percent).

Preparation of chloro(t-butylamino)dimethylsilane $Me_2SiCl_2$ (151.50 g, 1.17 moles) was stirred in pentane (2 L) as $N(C_2H_5)_3$ (119.62 g, 1.18 moles) was added slowly. t-Butylamine (85.85 g, 1.17 moles) in pentane (100 mL) was then added dropwise and the reaction allowed to stir at room temperature for 16 hours. After the reaction period the mixture was filtered and concentrated to 600 mL at which time more salts began to precipitate. The mixture was then refiltered and concentrated to 250 mL and then transferred to a 250 mL roundbottom flask equipped with a microdistillation apparatus and a thermometer. Distillation was performed until the reflux temperature reached 50° C. The clear, colorless liquid remaining was then determined to be pure by NMR and the yield to be essentially quantitative.

$^1$H NMR (300 MHZ, $CDCl_3$); δ0.31 (s, 6H), 1.10 (s, 6H), 1.89 (s, 1H).

Preparation of (2-methylindenyl)(t-butylamino)dimethylsilane

Chloro(t-butylamino)dimethylsilane (9.57 g, 0.058 moles) was stirred in diethylether (150 mL) at 0° C. as lithium-2-methylindenide (7.68 g, 0.058 moles) was added as a solid over a 15 minute period of time. The mixture was then allowed to stir for 16 hours at room temperature. After the reaction period the volatiles were removed and the residue extracted and filtered using hexane. Removal of the volatiles resulted in the isolation of the desired product as a pale yellow oil (9.99 g, 67.5 percent).

$^1$H NMR (300 MHZ, $CDCl_3$, TMS): δ−0.089 (s, 3H), 0.12 (s, 3H), 1.03 (s, 9H), 2.14 (s, 3H), 3.22 (s, 1H), 6.54 (s, 1H), 7.14–7.55 (m, 4H).

Preparation of $Li_2$[(2-methylindenyl)(t-butylamido)dimethylsilane]●0.75 $Et_2O$ (2-methylindenyl)(t-butylamino)dimethylsilane (5.00 g, 0.0192 moles) was stirred in diethylether (60 mL) as n-BuLi (0.0405 moles, 16.2 mL of 2.5 M solution in hexane) was added slowly. This mixture was then allowed to stir for 16 hours. After the reaction period the volatiles were removed and the residue washed with hexane and then collected as a solid via filtration which was used without further purification or analysis (5.70 g, 90.5 percent).

Preparation of (2-methylindenyl)dimethyl(t-butylamido)silanetitanium dichloride with $PbCl_2$ oxidation $Li_2$[(2-methylindenyl)(t-butylamido)dimethylsilane]●¾ $Et_2O$ (5.70 g, 0.0174 moles) was slowly added as a solid to a slurry of $TiCl_3(THF)_3$ (6.46 g, 0.0174 moles) in THF (80 mL). This mixture was allowed to stir for 45 minutes. $PbCl_2$ (2.76 g, 0.00995 moles) was then added to the mixture which was then allowed to stir for an additional 45 minutes. After the reaction period the volatiles were removed and the residue extracted and filtered using toluene. The toluene was then removed and the residue slurried in hexane and then collected as a red-brown crystalline solid by filtration. A second crop was obtained by concentrating and cooling the filtrate to −20° C. for 16 hours followed by a second filtration. The crops were then combined and determined to be the desired product (4.88 g, 74.2 percent).

$^1$H NMR (300 MHz, $C_6D_6$): δ0.42 (s, 3H), 0.56 (s, 3H), 1.34 (s, 3H), 2.14 (s, 9H), 6.71 (s, 1H), 6.92 (t, 1H), 7.04 (t, 1H), 7.25 (d, 1H, 7.59 (d, 1H).

Preparation of (2-methylindenyl)dimethyl(t-butylamido)titanium dichloride with methylene chloride oxidation $Li_2$[(2-methylindenyl)(t-butylamido)dimethylsilane]●$Et_2O$ (2.00 g, 0.00612 moles) and $TiCl_3(THF)_3$ (2.32 g, 0.00612 moles) were combined as solids. THF (100 mL) was then added to the mixture which was then allowed to stir for 30 minutes. $CH_2Cl_2$ (0.00306 moles) was then added and the mixture allowed to stir for an additional 2 hours. After the reaction period the volatiles were removed and the residue extracted and filtered using toluene through a Celite™ brand filter aid. The toluene was then removed and the residue washed with hexane resulting in the isolation of the desired product (0.900 g, 40 percent). Spectroscopic analysis was the same as described above.

Preparation of (2-methylindenyl)dimethyl(t-butylamido)silanetitanium dichloride from $TiCl_4$ $Li_2$[(2-methylindenyl)(t-butylamido)dimethylsilane]●0.75 $Et_2O$ (2.00 g, 0.00612 moles) was dissolved in THF (10 mL) and stirred as $TiCl_4(THF)_2$ (2.043 g, 0.00612 moles) in THF (15 mL) was added slowly. This mixture was allowed to stir for 2 hours. After the reaction period the volatiles were removed and the residue extracted and filtered using toluene through a Celite™ pad. The toluene was then removed and the residue washed with hexane resulting in the isolation of the desired product (1.43 g, 62 percent). Spectroscopic analysis was the same as described above.

Example 2

Preparation of (2-methylindenyl)dimethyl(t-butylamido)silanetitanium dimethyl

[(2-methylindenyl)dimethyl(t-butylamido)silane]$TiCl_2$ (0.800 g, 0.00211 moles) was stirred in diethylether (30 mL) as MeMgI (0.00454 moles, 1.50 mL 3.00 M solution in diethylether) was added dropwise. This mixture was then allowed to stir for 30 minutes. After the reaction period the volatiles were removed and the residue extracted and filtered using hexane. Removal of the volatiles resulted in the isolation of the desired product as a yellow solid (0.220 g, 30.8 percent).

$^1$H NMR (300 MHz, $C_6D_6$): δ−0.11 (s, 3H), 0.46 (s, 3H), 0.56 (s, 3H), 0.85 (s, 3H), 1.47 (s, 9H), 2.00 (s, 3H), 6.75 (s, 1H), 6.88 (t, 1H), 7.06 (t, 1H), 7.42 (d, 1H), 7.50 (d, 1H).

Example 3

Preparation of (2-methylinedenyl)dimethyl(t-butylamido)silanetitanium (II) (1,4-diphenyl-1,3-butadiene)

[(2-methylindenyl)dimethyl(t-butylamido)silane]$TiCl_2$ (2.20 g, 0.00583 moles) was slurried in hexane (150 mL) with 1,4-diphenyl-1,3-butadiene (1.20 g, 0.00583 moles) as n-BuLi (0.0117 moles, 4.67 mL of 2.5 M in hexane) was added slowly. This mixture was then refluxed for 2 hours. After the reaction period the mixture was cooled to room temperature and then filtered through Celite™. Removal of the volatiles resulted in the isolation of the desired product as a red/brown powder (1.81 g, 60.6 percent).

$^1$H NMR (250 MHz, $C_6D_6$, TMS): δ0.61 (s, 3H), 0.72 (s, 3H), 1.25 (s, 9H), 1.78 (s, 3H), 3.35 (d, 1H), 3.70 (d, 1H), 3.85 (m, 1H), 5.08 (m, 1H), 5.42 (s, 1H), 7.40–6.15 (m, 14H).

Example 4

Preparation of (3-methylindenyl)dimethyl(t-butylamido)silanetitanium dichloride

Preparation of 3-Methylindene

Lithium indenide (9.60 g, 0.0786 moles) in diethylether (100 mL) was added dropwise to a solution of dimethylsulfate (9.91 g, 0.0786 moles) in diethylether (125 mL) over a period of 15 minutes. After the addition was complete, $H_2O$ (150 mL) was added to the reaction. The organic layer was then separated and washed with $H_2O$ (2×100 mL). Drying over $MgSO_4$ followed by filtration and solvent removal yielded the desired product as a yellow oil (9.68 g, 94.7 percent).

$^1$H NMR (300 MHZ, $CDCl_3$, TMS): δ1.20 (d, 3H), 3.90 (q, 1H), 6.37 (dd, 1H), 6.68 (dd, 1H), 7.05–7.19 (m, 2H), 7.26 (d, 1H), 7.30 (d, 1H).

$^{13}$C NMR (75 MHz, $CDCl_3$): δ15.94, 45.07, 120.96, 122.56, 124.72, 126.35, 130.23, 141.27, 143.88, 149.16.

Preparation of Lithium-1-Methylindenide

3-Methylindene (9.68 g, 0.0745 moles) was stirred in hexane (300 mL) as nBuLi (0.0745 moles, 29.78 mL of 2.5 M solution in hexane) was added dropwise. The mixture was then allowed to stir for 48 hours at room temperature during which time a solid precipitated. After the reaction period the solid was collected via suction filtration as a light yellow powder which was used without further purification or analysis (9.38 g, 92.5 percent).

Preparation of (3-methylindenyl)(t-butylamine)dimethylsilane

Chloro(t-butylamino)dimethylsilane (5.47 g, 0.033 moles) was stirred in THF (200 mL) as lithium-1-methylindenide (4.51 g, 0.033 moles) in THF (50 mL) was added dropwise. This mixture was allowed to stir for 16 hours at room temperature. After the reaction period the volatiles were removed and the residue extracted and filtered using hexane. Removal of the hexane resulted in the isolation of the desired product as a yellow oil (7.24 g, 84.5 percent).

$^1$H NMR (300 MHz, $C_6D_6$): δ–0.077 (s, 3H), –0.053 (s, 3H), 1.05 (s, 9H), 2.15 (s, 3H), 3.41 (s, 1H), 6.31 (s, 1H), 7.14–7.64 (m, 5H).

Preparation of $Li_2$[(3-methylindenyl)(t-butylamido)dimethylsilane]●0.75 $Et_2O$ (3-methylindenyl)(t-butylamino)dimethylsilane (7.24 g, 0.0279 moles) was stirred in diethylether (75 mL) as n-BuLi (0.0586 moles, 23.40 mL of 2.5 M solution in hexane) was added slowly. This mixture was then allowed to stir for 16 hours. After the reaction period the volatiles were removed and the residue washed with hexane and then collected as a solid via filtration which was used without further purification or analysis (7.01 g, 76.9 percent).

Preparation of (3-methylindenyl)dimethyl(t-butylamido)silanetitanium dichloride $Li_2$[(1-methylindenyl)(t-butylamido)dimethylsilane]●0.75 $Et_2O$ (7.01 g, 0.0214 moles) was slowly added as a solid to a slurry of $TiCl_3(THF)_3$ (7.94 g, 0.0214 moles) in THF (75 mL). This mixture was allowed to stir for 45 minutes. $PbCl_2$ (2.98 g, 0.0107 moles) was then added to the mixture which was then allowed to stir for an additional 45 minutes. After the reaction period the volatiles were removed and the residue extracted and filtered using toluene. The toluene was then removed and the residue slurried in hexane and then collected as a red-brown crystalline solid by filtration. A second crop was obtained by concentrating and cooling the filtrate followed by a second filtration. The crops were then combined and determined to be the desired product (4.67 g, 57.9 percent).

$^1$H NMR (300 MHz, $C_6D_6$): δ0.36 (s, 3H), 0.55 (s, 3H), 1.32 (s, 9H), 2.37 (s, 3H), 6.08 (s, 1H), 6.97 (t, 1H), 7.11 (t, 1H), 7.27 (d, 1H), 7.55 (d, 1H).

Example 5

Preparation of (3-methylindenyl)dimethyl(t-butylamido)silanetitanium dimethyl

[(3-methylindenyl)dimethyl(t-butylamido)saline]$TiCl_2$ (0.500 g, 0.00132 moles) was stirred in diethylether (35 mL) as MeMgI (0.00292 moles, 1.00 mL 3.0 M solution in diethylether) was added dropwise. This mixture was then allowed to stir for 35 minutes. After the reaction period the volatiles were removed and the residue extracted and filtered using hexane. Removal of the volatiles followed by a repeat of the filtration again using hexane resulted in the isolation of the desired product as a yellow oil after the removal of the hexane (0.230 g, 51.3 percent).

$^1$H NMR (300 MHz, $C_6D_6$): δ–0.16 (s, 3H), 0.38 (s, 3H), 0.57 (s, 3H), 0.70 (s, 3H), 1.46 (s, 9H), 2.34 (s, 3H), 5.83 (s, 1H), 6.91 (t, 1H), 7.11 (t, 1H), 7.46 (d, 1H).

Example 6

Preparation of (2,3-dimethylindenyl)dimethyl(t-butylamido)silanetitanium dichloride Preparation of 2,3-Dimethylindene To a stirred solution of 15.02 g (103 mmoles) of (+/–)-2-methyl-1-indanone in 200 mL of anhydrous diethyl ether at –78° C. under an argon atmosphere was injected 50 mL of a 3.0 M methylMgI solution in ether (150 mmoles MeMgI). The reaction was allowed to slowly warm to room temperature over three hours and then it was heated at 35° C. for 1 hour. The reaction was poured into 1L of water, and concentrated HCl was slowly added until a pH of 1 was achieved. The mixture was transferred to a separatory funnel and shaken vigorously. The layers were separated, and the aqueous layer was extracted with ether. The combined organic layers were washed with water (1×500 mL), with aqueous $NaHCO_3$ (1×500 mL), and with saturated aqueous NaCl (1×500 mL). The organic layer was dried over anhydrous $MgSO_4$ and filtered. GC showed that some alcohol was still present so the mixture was stirred with approximately 100 ml of 10 weight percent aqueous HCl for 1 hour. The mixture was transferred to a separatory funnel, and the layers were separated. The organic phase was washed with water (1×200 mL), with aqueous $NaHCO_3$ (1×300 mL), and with saturated aqueous NaCl (1×250 mL). Drying over $MgSO_4$ followed by filtration and solvent removal yielded 14.7 g (99 percent) of 1,2-Dimethylindene.

$^1$H NMR (300 MHz, $CDCl_3$, TMS); δ7.4–7.0 (m, 4H, aromatic), 3.23 (s, 2H, allylic $CH_2$), 2.04 (s, 3H, $CH_3$), 2.01 (s, 3H, $CH_3$).

$^{13}$C NMR (75 MHz, $CDCl_3$): δ147.1, 141.9, 137.3, 132.1, 125.7, 123.3, 122.6, 117.6, 42.2, 13.6, 10.0.

GC-MS: calculated for $C_{11}H_{12}$ 144.09, found 144.10.

Preparation of Lithium-2,3-Dimethylindenide 2,3-Dimethylindene (24.11 g, 0.1659 moles) was stirred in hexane (400 mL) as n-BuLi (0.20 moles, 80.0 mL of 2.5 M solution in hexane) was added dropwise. The mixture was then allowed to stir for 16 hours at room temperature during which time a solid precipitated. After the reaction period the solid was collected via suction filtration as a white powder which was used without further purification or analysis (20.64 g, 82.3 percent).

Preparation of (2,3-dimethylindenyl)(t-butylamine) dimethylsilane

Chloro(t-butylamino)dimethylsilane (6.48 g, 0.039 moles) was stirred in THF (100 mL) as lithium-2,3-dimethylindenide (5.61 g, 0.037 moles) in THF (25 mL) was added dropwise. This mixture was allowed to stir for 16 hours at room temperature. After the reaction period the volatiles were removed and the residue extracted and filtered using hexane. Removal of the hexane resulted in the isolation of the desired product as a yellow oil (9.64 g, 94.7 percent).

$^1$H NMR (300 MHZ, CDCl$_3$, TMS): δ−0.062 (s, 3H), 0.043 (s, 3H), 0.58 (s, 1H), 1.18 (s, 9H), 2.09 (s, 3H), 2.18 (s, 3H), 3.33 (s, 1H), 7.07–7.28 (m, 3H), 7.44 (d, $^3J_{HH}$=7.4 Hz, 1H).

$^{13}$C NMR (75 MHz, CDCl$_3$): δ0.0040, 0.90, 10.38, 15.39, 33.96, 49.66, 50.60, 117.73, 122.22, 122.88, 124.42, 130.45, 140.38, 144.14, 146.47.

Preparation of Li$_2$[(2,3-dimethylindenyl)(t-butylamido) dimethylsilane]●0.75 Et$_2$O (2,3-dimethylindenyl)(t-butylamino)dimethylsilane (7.28 g, 0.0266 moles) was stirred in diethylether (80 mL) as n-BuLi (0.0559 moles, 22.4 mL of 2.5 M solution in hexane) was added slowly. This mixture was then allowed to stir for 16 hours. After the reaction period the volatiles were removed and the residue washed with hexane and then collected as a solid via filtration which was used without further purification or analysis (8.34 g, 92.0 percent).

Preparation of (2,3-dimethylindenyl)dimethyl(t-butylamido)silane-titanium dichloride Li$_2$[(2,3-dimethylindenyl)(t-butylamido)dimethylsilane]●0.75 Et$_2$O (8.34 g, 0.0245 moles) was slowly added as a solid to a slurry of TiCl$_3$(THF)$_3$ (9.07 g, 0.0245 moles) in THF (75 mL). This mixture was allowed to stir for 30 minutes. PbCl$_2$ (3.40 g, 0.0123 moles) was then added to the mixture which was then allowed to stir for an additional 30 minutes. After the reaction period the volatiles were removed and the residue extracted and filtered using toluene. The toluene was then removed and the residue slurried in hexane and then collected as a solid by filtration. A second crop was obtained by concentrating and cooling the filtrate followed by a second filtration. The crops were then combined and determined to be the desired product (2.87 g, 30.0 percent).

$^1$H NMR (300 MHz, C$_6$D$_6$): δ0.48 (s, 3H), 0.60 (s, 3H, 1.33 (s, 9H), 2.09 (s, 3H), 2.26 (s, 3H), 6.94–7.15 (m, 2H), 7.28 (d, 1H), 7.63 (d, 1H).

Example 7

Preparation of (2,3-dimethylindenyl)dimethyl(t-butylamido)silanetitanium dimethyl (2,3-dimethylindenyl)dimethyl(t-butylamido)silane TiCl$_2$ (0.750 g, 0.00191 moles) was stirred in diethylether (50 mL) as methylMgI (0.00402 moles, 1.34 mL 3.0 M solution in diethylether) was added dropwise. This mixture was then allowed to stir for 30 minutes. After the reaction period the volatiles were removed and the residue extracted and filtered using hexane. Removal of the volatiles followed by a repeat of the filtration again using hexane resulted in the isolation of the desired product as a yellow oil after the removal of the hexane (0.620 g, 92.1 percent).

$^1$H NMR (300 MHz, C$_6$D$_6$): δ−0.13 (s, 3H), 0.50 (s, 3H), 0.60 (s, 3H), 0.66 (s, 3H), 1.47 (s, 9H), 1.93 (s, 3H), 2.24 (s, 3H), 6.93 (t, 1H), 7.12 (t, 1H), 7.39 (d, 1H), 7.55 (d, 1H).

Example 8

Preparation of (2,3-dimethylindenyl)dimethyl(cyclododecylamido)silanetitanium dichloride Preparation of Li$_2$[(2,3-dimethylindenyl)(cyclododecylamido)dimethyl-silane]0.75 Et$_2$O (2,3-dimethylindenyl)(cyclododecylamido) dimethylsilane (5.47 g, 0.0142 moles) was stirred in diethylether (25 mL) as n-BuLi (0.030 moles, 11.94 mL of 2.5 M solution in hexane) was added slowly. This mixture was then allowed to stir for 16 hours. After the reaction period the volatiles were removed and the residue washed with hexane and then collected as a solid via filtration which was used without further purification or analysis (5.47 g, 85.2 percent).

Preparation of (2,3-dimethylindenyl)dimethyl (cyclododecylamido)-silanetitanium dichloride Li$_2$[(2,3-dimethylindenyl)(cyclododecylamido) dimethylsilane]●¾Et$_2$O (5.47 g, 0.0121 moles) was slowly added as a solid to a slurry of TiCl$_3$(THF)$_3$(4.48 g, 0.0121 moles) in THF (75 mL). This mixture was allowed to stir for 45 minutes. PbCl$_2$ (1.68 g, 0.00604 moles) was then added to the mixture which was then allowed to stir for an additional 45 minutes. After the reaction period the volatiles were removed and the residue extracted and filtered using toluene. The toluene was then removed and the residue slurried in hexane and then collected as a red-brown crystalline solid by filtration. A second crop was obtained by concentrating and cooling the filtrate followed by a second filtration. The crops were then combined and determined to be the desired product (0.457 g, 7.6 percent).

$^1$H NMR (300 MHz, C$_6$D$_6$): δ0.52 (s, 3H), 0.63 (s, 3H), 1.15–1.91 (m, 23H), 2.11 (s, 3H), 2.23 (s, 3H), 5.31 (m, 1H), 6.83–7.12 (m, 2H), 7.29 (d, 1H), 7.63 (d, 3H).

Example 9

Preparation of (2,3-dimethylindenyl)dimethyl(cyclododecylamido)silanetitanium dimethyl (2,3-dimethylindenyl)dimethyl(cyclododecylamido) silane TiCl$_2$ (0.200 g, 0.000400 moles) was stirred in diethylether (50 mL) as methylMgI (0.00084 moles, 0.28 mL 3.0 M solution in diethylether) was added dropwise. This mixture was then allowed to stir for 30 minutes. After the reaction period the volatiles were removed and the residue extracted and filtered using hexane. Removal of the volatiles followed by a repeat of the filtration again using hexane resulted in the isolation of the desired product as an orange crystalline solid after the removal of the hexane (0.134 g, 73.2 percent).

$^1$H NMR (300 MHz, C$_6$D$_6$): δ−0.11 (s, 3H), 0.53 (s, 3H), 0.61 (s, 3H), 0.65 (s, 3H), 1.10–1.90 (m, 23H), 1.98 (s, 3H), 2.26 (s, 3H), 5.12–5.25 (m, 1H), 6.91 (t, 1H), 7.09 (t, 1H), 7.45 (d, 1H), 7.58 (d, 1H).

Example 10

Preparation of (2-ethylindenyl)dimethyl(t-butylamido)silanetitanium dichloride

Preparation of 2-Ethylindene

2-Bromoindene (8.1235 g, 0.04211 moles) and Ni(dppp)$Cl_2$ (0.1536 g, 2.83×10$^{-4}$ moles) were stirred in diethylether (100 mL) at −78° C. under a nitrogen atmosphere as ethylMgBr (0.045 moles, 15.00 mL of 3.0 M solution in diethylether) was added. The dry-ice bath was then removed and the reaction mixture allowed to warm to room temperature. The reaction mixture started off as a heterogeneous brick-red color and then turned to a homogeneous yellow/gold solution and then back to the heterogeneous brick-red mixture during the course of the warm-up. Gas chromatographic analysis after 2 hours of stirring at room temperature showed that the reaction was substantially quantitative. After the reaction period the mixture was poured onto ice and then extracted with 1 M HCL (1×100 mL) and 1 M $NaHCO_3$ (1×100 mL) and then dried with $MgSO_4$ and filtered. The desired product was isolated as a light yellow oil (5.65 g, 93.1 percent).

$^1$H NMR (300 MHz, $CDCl_3$, TMS): δ1.31 (t, $^3J_{HH}$=7.4 Hz, 3H), 2.59 (q, $^3J_{HH}$=7.4 Hz, 2H), 3.39 (s, 2H), 6.59 (s, 1H), 7.16–7.38 (m, 3H), 7.46 (d, $^3J_{HH}$=7.4 Hz, 1H).

$^{13}$C NMR (75 MHz, $CDCl_3$): δ13.65, 24.63, 41.23, 119.96, 123.47, 123.60, 125.25, 126.29, 143.12, 145.76, 152.47.

GC-MS: Calculated for $C_{11}H_{12}$ 144.22, found 144.10.

Preparation of Lithium-2-Ethylindenide

2-Ethylindene (7.10 g, 0.049 moles) was stirred in hexane (100 mL) as n-BuLi (0.050 moles, 25.00 mL of 2.0 M solution in cyclohexane) was added dropwise. The mixture was then allowed to stir for 16 hours at room temperature during which time a solid precipitated. After the reaction period the solid was collected via suction filtration as a light yellow powder which was used without further purification or analysis (5.21 g, 70.5 percent).

Preparation of (2-ethylindenyl)(t-butylamine)dimethylsilane

Chloro(t-butylamino)dimethylsilane (6.0038 g, 0.03623 moles) was stirred in THF (100 mL) as lithium-2-ethylindenide (4.96 g, 0.033 moles) in THF (25 mL) was added dropwise. This mixture was allowed to stir for 16 hours at room temperature. After the reaction period the volatiles were removed and the residue extracted and filtered using hexane. Removal of the hexane resulted in the isolation of the desired product as a yellow oil (8.64 g, 95.7 percent).

$^1$H NMR (300 MHz, $CDCl_3$): δ0.067 (s, 3H), 0.085 (s, 3H), 1.18 (s, 9H), 1.25 (t, $^3J_{HH}$=7.5 Hz, 3 H), 2.46–2.54 (m, 1H), 2.54–2.82 (m, 1H), 3.47 (s, 1H), 6.57 (s, 1H), 7.04–7.45 (m, 4H).

Preparation of $Li_2$[(2-ethylindenyl)(t-butylamido)dimethylsilane]●0.75 $Et_2O$ (2-ethylindenyl)(t-butylamino)dimethylsilane (7.24 g, 0.026 moles) was stirred in diethylether (50 mL) as n-BuLi (0.0556 moles, 22.2 mL of 2.50 M solution in hexane) was added slowly. This mixture was then allowed to stir for 16 hours. After the reaction period the volatiles were removed and the residue washed with hexane and then collected as a solid via filtration which was used without further purification or analysis (6.79 g, 75.2 percent).

Preparation of (2-ethylindenyl)dimethyl(t-butylamido)silanetitanium dichloride $Li_2$[(2-ethylindenyl)(t-butylamido)dimethylsilane]●0.75 $Et_2O$ (6.79 g, 0.0199 moles) was slowly added as a solid to a slurry of $TiCl_3(THF)_3$ (7.37 g, 0.0199 moles) in THF (75 mL). This mixture was allowed to stir for 45 minutes. $PbCl_2$ (2.76 g, 0.00995 moles) was then added to the mixture which was then allowed to stir for an additional 45 minutes. After the reaction period the volatiles were removed and the residue extracted and filtered using toluene. The toluene was then removed and the residue slurried in hexane and then collected as a red-brown crystalline solid by filtration. A second crop was obtained by concentrating and cooling the filtrate followed by a second filtration. The crops were then combined and determined to be the desired product (3.15 g, 40.6 percent).

$^1$H NMR (300 MHz, $C_6D_6$): δ0.45 (s, 3H), 0.57 (s, 3H), 1.19 (t, 3H), 1.34 (s, 9H), 2.43–2.70 (m, 2H), 6.81 (s, 1H), 6.90–7.09 (m, 2H), 7.28 (d, 1H), 7.62 (d, 1H).

Example 11

Preparation of (2-ethylindenyl)dimethyl(t-butylamido)silanetitanium dimethyl (2-ethylindenyl)dimethyl(t-butylamido)silane $TiCl_2$ (0.500 g, 0.00128 moles) was stirred in diethylether (50 mL) as MeMgI (0.00269 moles, 0.900 mL 3.0 M solution in diethylether) was added dropwise. This mixture was then allowed to stir for 30 minutes. After the reaction period the volatiles were removed and the residue extracted and filtered using hexane. Removal of the volatiles followed by a repeat of the filtration again using hexane resulted in the isolation of the desired product as a yellow oil after the removal of the hexane (0.310 g, 69.2 percent).

$^1$H NMR (300 MHz, $C_6D_6$): δ−0.11 (s, 3H), 0.49 (s, 3H), 0.57 (s, 3H), 0.83 (s, 3H), 1.14 (t, 3H), 1.47 (s, 9H), 2.20–2.34 (m, 1H), 2.36–2.51 (m, 1H), 6.83 (s, 1H), 6.85–6.94 (m, 1H), 7.03–7.12 (m, 1H), 7.46 (d, 1H), 7.53 (d, 1H).

Example 12

Preparation of (2-propylindenyl)dimethyl(t-butylamido)silanetitanium dichloride

Preparation of 2-Propylindene

To an oven-dried 250 mL round bottom flask containing a magnetic stir bar and equipped with a reflux condenser and vacuum adapter was added 2-bromoindene (15.0 g, 76.9 mmol) and Ni(dppp)$Cl_2$ (0.42 g, 0.77 mmol) (dppp=1,3-bis(diphenyl-phosphino)propane). The flask was stoppered and evacuated. Deoxygenated anhydrous diethyl ether (150 mL) was added via cannula under argon at −78° C. The reaction was stirred under argon without exterior cooling as 42 mL of a 2.0 M propylmagnesium chloride in ether solution was added via syringe (84 mmol propylmagnesium chloride). The reaction was placed in a dry ice/acetone bath when a vigorous reflux was achieved. The dry ice/acetone bath was removed after 2 minutes, and the reaction was stirred at room temperature under argon for 90 minutes. The reaction was carefully poured into water and 10 weight percent aqueous HCl was added until the mixture was acidic. The mixture was extracted with ether (3×200 mL), and the combined organic layers were washed with water (1×250 mL), with aqueous sodium bicarbonate (1×250 mL), and with aqueous saturated sodium chloride solution (1×250 mL). Drying over anhydrous sodium sulfate followed by filtration and solvent removal yielded 12.14 g (99.7 percent) of the desired product.

$^1$H NMR (300 MHz, $CDCl_3$, TMS): δ7.4–7.0 (m, 4H), 6.48 (s, 1H), 3.26 (s, 2H), 2.43 (t, $^3J_{HH}$=7.4 Hz, 2H), 1.61 (s, $^3J_{HH}$=7.4 Hz, 2H), 0.96 (t, $^3J_{HH}$=7.4 Hz, 3H).

$^{13}$C NMR (75 MHz, $CDCl_3$), δ150.17, 145.46, 142.83, 126.03, 125.96, 123.30, 123.10, 119.64, 40.81, 33.23, 22.15, 13.95.

GC-MS: Calculated for $C_{12}H_{14}$ 158.11, found 158.05.

Preparation of Lithium-2-Propylindenide

2-Propylindene (11.0 g, 0.069 moles) was stirred in hexane (500 mL) as n-BuLi (0.076 moles, 30.6 mL of 2.5 M solution in hexane) was added dropwise. The mixture was then allowed to stir for 16 hours at room temperature during which time a solid precipitated. After the reaction period the solid was collected via suction filtration as a light yellow powder which was used without further purification or analysis (10.8 g, 94.3 percent).

Preparation of (2-propylindenyl)(t-butylamino) dimethylsilane

Dimethylsilyl(t-butylamino)chloride (3.03 g, 0.018 moles) was stirred in THF (100 mL) as lithium-2-propylindenide (3.00 g, 0.018 moles) in THF (20 mL) was added dropwise. This mixture was allowed to stir for 16 hours at room temperature. After the reaction period the volatiles were removed and the residue extracted and filtered using hexane. Removal of the hexane resulted in the isolation of the desired product as a yellow oil (4.67 g, 89.0 percent). This compound was used without further purification or analysis.

Preparation of $Li_2$[(2-propylindenyl)(t-butylamido) dimethylsilane]•¾ $Et_2O$ (2-propylindenyl)(t-butylamino)dimethylsilane (4.67 g, 0.0162 moles) was stirred in diethylether (75 mL) as n-BuLi (0.0341 moles, 13.70 mL of 2.50 M solution in hexane) was added slowly. This mixture was then allowed to stir for 16 hours. After the reaction period the volatiles were removed and the residue washed with hexane and then collected as a solid via filtration which was used without further purification or analysis (4.92 g, 85.3 percent).

Preparation of (2-propylindenyl)dimethyl(t-butylamido)silanetitanium Dichloride $Li_2$[(2-propylindenyl)(t-butylamido)dimethylsilane]•¾ $Et_2O$ (4.92 g, 0.0138 moles) was slowly added as a solid to a slurry of $TiCl_3(THF)_3$ (5.12 g, 0.0138 moles) in THF (75 mL). This mixture was allowed to stir for 45 minutes. $PbCl_2$ (1.92 g, 0.00691 moles) was then added to the mixture which was then allowed to stir for an additional 45 minutes. After the reaction period the volatiles were removed and the residue extracted and filtered using toluene. The toluene was then removed and the residue slurried in hexane and then collected as a red-brown crystalline solid by filtration. A second crop was obtained by concentrating and cooling the filtrate followed by a second filtration. The crops were then combined and determined to be the desired product (2.20 g 39.4 percent).

$^1$H NMR (300 MHz, $C_6D_6$): δ0.49 (s, 3 H), 0.58 (s, 3 H), 0.80 (t, 3 H), 1.35 (s, 9 H), 1.47–1.64 (m, 2 H), 2.51–2.73 (m, 2 H), 6.83 (s, 1 H), 6.93 (t, 1 H), 7.05 (t, 1 H), 7.29 (d, 1 H), 7.63 (d, 1 H)

EXAMPLE 13

Preparation of (2-propylindenyl)dimethyl(t-butylamido)silanetitanium Dimethyl (2-propylindenyl)dimethyl(t-butylamido)silane $TiCl_2$ (0.500 g, 0.00124 moles) was stirred in diethylether (50 mL) as MeMgI (0.00260 moles, 0.870 mL 3.0 M solution in diethylether) was added dropwise. This mixture was then allowed to stir for 30 minutes. After the reaction period the volatiles were removed and the residue extracted and filtered using hexane. Removal of the volatiles followed by a repeat of the filtration again using hexane resulted in the isolation of the desired product as a yellow oil after the removal of the hexane (0.340 g, 75.6 percent).

$^1$H NMR (300 MHz, $C_6D_6$): d-0.11 (s, 3 H), 0.52 (s, 3 H), 0.57 (s, 3 H), 0.85 (t, 3 H), 1.48 (s, 9 H), 1.56–1.70 (m, 2 H) 2.20–2.32 (m, 1 H), 2.40–2.52 (m, 1 H), 6.84 (s, 1 H), 6.90 (t, 1 H), 7.08 (t, 1 H), 7.46 (d, 1 H), 7.53 (d, 1 H).

EXAMPLE 14

Preparation of (2-methyl-4-phenylindenyl)dimethyl (t-butylamido)silanetitanium Dichloride Preparation of (2-methyl-4-phenylindenyl)(t-butylamino)dimethylsilane 2-methyl-4-phenylindene (synthesized substantially according to the technique reported in U.S. Pat. No. 5,329.033) (3.00 g, 0.014 moles) in THF (10 mL) was added dropwise to a stirring solution of KH (0.601 g, 0.0150 moles) in THF (50 mL). This mixture was allowed to stir for 16 hours. The solution was then filtered and added dropwise to a solution of dimethylsilyl(t-butylamino)chloride (2.41 g, 0.0145 moles) in THF (75 mL). This mixture was allowed to stir for 16 hours. After the reaction period the volatiles were removed and the residue extracted and filtered using hexane. Removal of the volatiles resulted in the isolation of the desired product as a light yellow oil (4.00 g, 82.0 percent).

$^1$H NMR (300 MHz, $CDCl_3$): δ–0.0056 (s, 3 H), 0.18 (s, 3 H), 1.21 (s, 9 H), 1.46 (s, 1 H), 2.29 (s, 3 H), 3.50 (s, 1 H), 6.73 (s, 1 H), 7.11–7.61 (m, 8 H).

Preparation of (2-methyl-4-phenylindenyl)dimethyl (t-butylamido)-silanetitanium Dichloride (2-methyl-4-phenylindenyl)(t-butylamino)dimethylsilane (1.13 g, 0.00338 moles) was stirred in diethylether (50 mL) as n-BuLi (0.00676 moles, 2.71 mL of 2.50 M solution on hexane) was added dropwise. This solution was allowed to stir for 3 hours and then added dropwise to a slurry of $TiCl_3(THF)_3$ (1.25 g, 0.00338 moles) in THF (75 mL). This solution was then allowed to stir for 3 hours. Methylene chloride (0.50 mL) was then added to the solution which was allowed to stir for an additional 30 minutes. After the reaction period the volatiles were removed and the residue extracted and filtered using hexane. The removal of the hexane resulted in the isolation of a dark residue which was then redissolved in THF (50 mL) and stirred with $PbCl_2$ (1.0186 g, 0.003663 moles) for 30 minutes. After the reaction period the volatiles were removed and the mixture extracted and filtered using hexane. Concentration of this solution and subsequent cooling to −78° C. resulted in the isolation of the desired product as a red/brown crystalline solid (0.8493 g, 55.5 percent)

$^1$H NMR (300 MHz, $C_6D_6$): δ0.43 (s, 3 H), 0.60 (s, 3 H), 1.36 (s, 9 H), 2.09 (s, 3 H), 6.98–7.29 (m, 7 H), 7.61 (d, 1 H), 7.67 (d, 1 H)

EXAMPLE 15

Preparation of (2-methyl-4-phenylindenyl)dimethyl (t-butylamido)silanetitanium Dimethyl (2-methyl-4-indenyl)dimethyl(t-butylamido)silane $TiCl_2$ (0.254 g, 0.000563 moles) was stirred in toluene (50 mL) at 0° C. as MeMgBr (0.00113 moles, 0.38 mL of 3.0 M solution in diethylether) was added dropwise. This mixture was then allowed to stir for 16 hours. After the reaction period the volatiles were removed and the residue extracted and filtered using hexane. Removal of the hexane result in the isolation of the desired product as an amorphous solid (0.149 g, 64.3 percent).

$^1$H NMR (300 MHz, C$_6$D$_6$): δ0.029 (s, 3 H), 0.48 (s, 3 H), 0.61 (s, 3 H), 0.86 (s, 3 H), 1.49 (s, 9 H), 1.96 (s, 3 H), 6.90–7.35 (m, 7 H), 7.53 (d, 1 H), 7.67 (d, 1 H)

EXAMPLE 16

Preparation of (η$^5$-2,3,4,6,7-pentamethylindenyl) dimethyl-(t-butylamido)silanetitanium Dichloride Preparation of E-1-(2,3,5,6-tetramethylphenyl)-2-methyl-2-buten-1-ol Lithium mesitylene (7.55 g, 0.0588 moles) was slurried in diethylether (50 mL) at 0° C. as trans-2-methyl-2-butenol (5.04 g, 0.0588 moles) was added dropwise. This solution was then allowed to stir for 16 hours at room temperature. After the reaction period the mixture was poured onto ice water, the organic layer separated and washed with water, and then dried over MgSO$_4$. Filtration and removal of the volatiles followed by recrystallization from hexane resulted in the isolation of the desired product (5.88 g, 57.4 percent).

$^1$H NMR (300 MHz, CDCl$_3$, TMS): δ1.40–1.66 (m, 6 H), 1.82 (br, 1 H), 2.25 (s, 3 H), 2.31 (s, 6 H), 5.41–5.51 (m, 1 H), 6.81 (s, 1 H)

GC-MS: Calculated for C$_{14}$H$_{20}$O 204.32, found 204.15.

Preparation of 1,2,4,5,7-pentamethylindene

Preparation of E-1-(2,3,5,6-tetramethylphenyl)-2-methyl-2-buten-1-ol (1.50 g, 0.00734 moles) in hexane (20 mL) was added dropwise to concentrated H$_2$SO$_4$ (20 mL) at 0° C. The resulting red solution was then allowed to warm to room temperature and then quenched by adding the solution dropwise to a solution of Na$_2$CO$_3$ (300 mL of 1.89 M solution) at 0° C. The organic layer was then separated and the aqueous layer extracted with pentane (3×100 mL). The organic layers were then combined and dried over MgSO$_4$ followed by filtration and solvent removal resulting in the isolation of the desired product (1.22 g, 89.7 percent).

$^1$H NMR (300 MHz, CDCl$_3$): δ1.55 (s, 3 H), 2.04 (s, 3 H), 2.24 (s, 3 H), 2.28 (s, 3 H), 2.46 (s, 3 H), 3.07 (s, 2 H), 6.75 (s, 1 H)

Preparation of Lithium-2,3,4,5,7-pentamethylindenide 1,2,4,5,7-pentamethylindene (1.22 g, 0.00655 moles) was stirred in pentane (250 mL) as n-BuLi (0.00655 moles, 2.61 mL of 2.50 M solution in hexane) was added dropwise. The mixture was then allowed to stir for 48 hours at room temperature during which time a solid precipitated. After the reaction period the solid was collected via suction filtration which was used without further purification or analysis (1.07 g, 85.6 percent).

Preparation of (2,3,4,6,7-pentamethylindenyl)(t-butylamino)dimethyl-silane

Choloro(t-butylamino)dimethylsilane (0.922 g, 0.0556 moles) was stirred in THF (50 mL) as lithium-2,3,4,6,7-pentamethylindenide (1.07 g, 0.0556 moles) in THF (20 mL) was added dropwise. This mixture was then refluxed for 30 minutes and then allowed to stir to room temperature. After the reaction period the volatiles were removed and the residue extracted and filtered using hexane. Removal of the hexane resulted in the isolation of the desired product as (1.76 g, 99.9 percent).

GC-MS: Calculated for C$_{20}$H$_{33}$NSi 315.58, found 315.25.

Preparation of Li$_2$[(2,3,4,6,7-pentamethylindenyl)(t-butylamido)-dimethylsilane]•0.75 Et$_2$O (2,3,4,6,7-pentamethylindenyl)(t-butylamino) dimethylsilane (1.76 g, 0.00558 moles) was stirred in diethylether (35 mL) as n-BuLi (0.0112 moles, 4.46 mL of 2.50 M solution in hexane) was added slowly. This mixture was then allowed to stir for 16 hours. After the reaction period the volatiles were removed and the residue washed with hexane and then collected as a solid via filtration which was used without further purification or analysis (1.32 g, 72.1 percent).

Preparation of (2,3,4,6,7-pentamethylindenyl) dimethyl(t-butylamido)-silanetitanium Dichloride Li$_2$[(2,3,4,6,7-pentamethylindenyl)(t-butylamido) dimethylsilane]•0.75 Et$_2$O (1.32 g, 0.0403 moles) was slowly added as a solid to a slurry of TiCl$_3$(THF)$_3$ (1.49 g, 0.0403 moles) in THF (75 mL). This mixture was allowed to stir for 45 minutes. PbCl$_2$ (0.560 g, 0.00201 moles) was then added to the mixture which was then allowed to stir for an additional 45 minutes. After the reaction period the volatiles were removed and the residue extracted and filtered using pentane. The pentane extract was then concentrated and cooled to −20° C., followed by the collection of the desired product as a red/brown microcrystalline material via filtration (0.33 g, 19 percent).

$^1$H NMR (300 MHz, C$_6$D$_6$): δ0.56 (s, 3 H), 0.62 (s, 3 H), 1.39 (s, 9 H), 2.10 (s, 3 H), 2.16 (s, 3 H), 2.30 (s, 3 H), 2.37 (s, 3 H), 2.53 (s, 3 H), 6.71 (s, 1 H)

EXAMPLE 17

Preparation of (2,3,4,6,7-pentamethylindenyl) dimethyl(t-butylamido)silanetitanium Dimethyl (2,3,4,6,7-pentamethylindenyl)dimethyl(t-butylamido) silane TiCl$_2$ (0.243 g, 0.000562 moles) was stirred in diethylether (30 mL) as MeMgI (0.00112 moles, 0.380 mL 3.00 M solution in diethylethen was added dropwise. This mixture was then allowed to stir for 30 minutes. After the reaction period the volatiles were removed and the residue extracted and filtered using pentane. Removal of the pentane resulted in the isolation of the desired product as a yellow solid (0.181 g, 82.3 percent).

$^1$H NMR (300 MHz, C$_6$D$_6$): δ−0.14 (s, 3 H), 0.57 (s, 3 H), 0.61 (s, 3 H), 0.63 (s, 3 H), 1.50 (s, 9 H), 1.99 (s, 3 H), 2.14 (s, 3 H), 2.23 (s, 3 H), 2.38 (s, 3 H), 2.46 (s, 3 H), 6.66 (s, 1 H).

EXAMPLE 18

Preparation of (2,3-dimethylindenyl)dimethyl(t-butylamido)silanetitanium (III) 2-(N,N-dimethyl) aminobenzyl In the drybox 0.543 g (1.5 mmol) of TiCl$_3$(THF)$_3$ was stirred in approximately 60 ml of THF. Dilithium (N-t-butylamido)(dimethyl)(2,3-dimethylindenyl)silane (¾ Et$_2$O) (0.50 g, 1.5 mmol) was added as a solid while stirring. Stirring was continued for 15 minutes, then 0.207 g (1.5 mmol) of lithium (2-N,N-dimethylamino)benzyl was added and stirring continued for 30 more minutes. The THF was then removed under reduced pressure. Hexane was added to the residue. The brown/red precipitate was collected via filtration and washed with cold hexane. The solid product was dried under reduced pressure to yield 0.593 g (89.2 percent) of product.

EXAMPLE 19

Preparation of (2,3-dimethylindenyl)dimethyl (adamantyl-amido)silanetitanium Dichloride Preparation of Lithium-1-adamantanamide 1-Adamantanamine (14.1 g, 0.0931 moles) was stirred in hexane (300 mL) as n-BuLi (0.0978 moles, 39.0 ml of 2.50 M solution in hexane) was added dropwise. The mixture was allowed to stir for 16 hours at room temperature during which time a solid precipitated. After the reaction period the solid was collected via suction filtration as a white solid which was used without further purification or analysis (13.4 g, 91.9 percent).

Preparation of (1-acamantylamino) chlorodimethylsilane

In the drybox 20.53 g of dichlorodimethylsilane (20.5 g, 0.159 moles) was stirred in THF (150 mL) as lithium-1-adamantanamide (10.0 g, 0.064 moles) in THF (100 mL) was added slowly as a slurry. This mixture was allowed to stir for 2.5 hours at room temperature. After the reaction period the volatiles were removed and the residue extracted and filtered using hexane. Removal of the hexane resulted in the isolation of the desired product as a white solid (14.3 g, 92.1 percent).

$^1$H NMR (300 MHz, CDCl$_3$): δ0.46 (s, 6 H), 1.28 (br, 1 H), 1.62 (s, 6 H), 1.74 (s, 6 H), 2.04 (s, 3 H).

$^{13}$C NMR (75 MHz, CDCl$_3$): δ4.97, 30.12, 36.41, 46.74, 50.67.

Preparation of (2,3-dimethylindenyl)(1-adamantylamino)dimethylsilane (1-adamantylamino)chlorodimethylsilane (5.48 g, 0.0225 moles) was stirred in THF (100 mL) as lithium 2.3-dimethylindenide (3.40 g, 0.0225 moles) in THF (25 mL) was added dropwise. This mixture was allowed to stir for 8 hours. After the reaction period the volatiles were removed and the residue extracted and filtered using hexane. Removal of the hexane resulted in the isolation of the desired product as a solid. (7.69 g, 97.0 percent).

$^1$H NMR (300 MHz, CDCl$_3$): δ–0.053 (s, 3 H), 0.022 (s, 3 H), 1.61 (s, 6 H), 1.66 (s, 6 H), 2.03 (s, 3 H), 2.08 (s, 3 H), 2.18 (s, 3 H), 3.33 (s, 1 H), 7.04–7.27 (m, 3 H), 7.45 (d, $^3J_{HH}$=7.4 Hz, 1 H). The proton for the amine could not be resolved from the rest of the spectrum.

Preparation of Dilithio [(2,3-dimethylindenyl)(1-adamantylamido)-dimethylsilane]

(2,3-dimethylindene)(1-adamantylamino)dimethylsilane (7.69 g, 0.0218 moles) was stirred in hexane (150 mL) as n-BuLi (0.0436 moles, 17.4 mL of 2.50 M solution in hexane) was added slowly. This mixture was then allowed to stir for 16 hours. After the reaction period the mxiture was filtered and the desired product isolated as a pale yellow powder which was used without further purification or analysis (7.68 g, 96.6 percent).

Preparation of (2,3-dimethylindenyl)dimethyl(1-adamantylamido)silane-titanium Dichloride Dilithio (2,3-dimethylindenyl)(1-adamantylamido) dimethylsilane (7.68 g, 0.0211 moles) in THF (50 mL) was added dropwise to a slurry of TiCl$_3$(THF)$_3$ (7.81 g, 0.0211 moles) in THF (100 mL). This mixture was allowed to stir for three hours. PbCl$_2$ (3.18 g, 0.0114 moles) was then added to the mixture which was then allowed to stir for an additional hour. After the reaction period the volatiles were removed and the residue extracted and filtered using toluene. The toluene was then removed and the residue slurried in hexane and then cooled to −15° C. The desired product was then collected as a red-brown crystalline solid by filtration (7.70 g, 77.9 percent).

$^1$H NMR (300 MHz, C$_6$D$_6$): δ0.55 (s, 3 H), 0.67 (s, 3 H), 1.49 (q, $^3J_{HH}$=10.6 Hz, 6 H), 1.93 (s, 3 H), 2.02 (s, 6 H), 2.14 (s, 3 H), 2.30 (s, 3 H), 7.01 (t, $^3J_{HH}$=7.2 Hz, 1 H), 7.13 (t, $^3J_{HH}$=8.3 Hz, 3 H), 7.31 (d, $^3J_{HH}$=8.5 Hz, 1 H), 7.69 (d, $^3J_{HH}$=8.6 Hz, 1 H).

EXAMPLE 20

Preparation of (2,3-dimethylindenyl)dimethyl)1-adamantylamidosilanetitanium Dimethyl (2,3-dimethylindenyl)dimethyl(1-adamantylamido) silanetitanium dichloride (0.300 g, 0.000640 moles) was stirred in THF (60 mL) as MeMgBr (0.00192 moles, 1.40 mL of a 1.40 M solution in toluene/THF) was added dropwise. This mixture was then allowed to stir for 1 hour. After the reaction period the volatiles were removed and the residue extracted and filtered using hexane. Removal of the hexane resulted in the isolation of the desired product as a yellow solid (0.228 g, 83.2 percent).

$^1$H NMR (300 MHz, C$_6$D$_6$): δ–0.079 (s, 3 H), 0.57 (s, 3 H), 0.66 (s, 3 H), 0.71 (s, 3 H), 1.61 (br s, 6 H), 1.98 (s, 3 H), 2.03 (br s, 3 H), 2.11 (s, 6 H), 2.27 (s, 3 H), 6.96 (t, $^3J_{HH}$=7.4 Hz, 1 H), 7.09–7.21 (m, 1 H), 7.41 (d, $^3J_{HH}$=8.2 Hz, 1 H), 7.60 (d, $^3J_{HH}$=8.3 Hz, 1 H).

Polymrizations

A two-liter Parr reactor was charged with 740 g of Isopar-E™ mixed alkanes solvent (available from Exxon Chemicals Inc.) and 118 g of 1-octene comonomer. Hydrogen was added as a molecular weight control agent by differential pressure expansion from a 75 mL addition tank at 25 psi (2070 kPa). The reactor was heated to the polymerization temperature of 140° C. and saturated with ethylene at 500 psig (3.4 MPa). 2.0 μmol each of catalyst and cocatalyst at 0.005 M solutions in toluene were premixed in the drybox. After the desired premix time, the solution was transferred to a catalyst addition tank and injected into the reactor. The polymerization conditions were maintained for 15 minutes with ethylene on demand. The resulting solution was removed from the reactor, and a hindered phenol antioxidant (Irganox™ 1010 from Ciba Geigy Corporation) was added to the resulting solution. Polymers formed were dried in a vacuum oven set at 120° C. for 20 hours. Results are contained in Table 1.

TABLE 1

| Run | Complex | Cocatalyst | MI (dg/min)$^3$ |
| --- | --- | --- | --- |
| 1 | Ex. 2 | TPFPB$^2$ | 0.4 |
| 2 | Ex. 5 | " | 0.8 |
| 3 | Ex. 7 | " | 0.8 |
| 4 | Ex. 11 | " | 1.1 |
| 5 | Ex. 13 | " | 1.2 |
| 6 | Ex. 15 | " | 3.3 |
| 7 | Ex. 17 | " | 1.0 |

TABLE 1-continued

| Run | Complex | Cocatalyst | MI (dg/min)[3] |
|---|---|---|---|
| 8 | Ex. 20 | " | 0.9 |
| 9* | TTTD[1] | " | 4.5 |

*Comparative, not an example of the invention
[1]-(tetramethylcyclopentadienyl)dimethyl(t-butylamido)silanetitanium dimethyl
[2]-trispentafluorophenylborane
[3]-melt index, $I_2$, measured in accordance with ASTM D-1238 (190/2.16)

Efficiencies in runs 1–8 of the above polymerizations average approximately 80 percent of those attained in comparative run 9. The results of the above polymerixations indicate that significantly higher molecular weight polymers are formed by the use of the present, substituted indenyl containing metal complexes compared to previously known constrained geometry or amidosilane bridge monocyclopentadienyl based metal complexes at the same reaction conditions. Such a result is highly desirable, particularly in a solution polymerizaton reaction, due to the fact that the operator is now able to obtain a given molecular weight polymer at a higher reaction temperature, thereby increasing productivity and reducing processing costs. Moreover, previously unattainable, low melt index, high comonomer content, high molecular weight, ethylene/α-olefin copolymers, especially EP and EPDM copolymers can be readily produced using such catalyst systems.

EXAMPLE 21

Preparation of (2,3,4,6-tetramethylindenyl)dimethyl (t-butylamido)silanetitanium Dimethyl Preparation of 2,4,6-Trimethylindanone m-Xylene (34.1 g, 0.32 moles) and 2-bromoisobutyryl bromide (73.9 g, 0.32 moles) were stirred in methylene chloride (500 mL) at 0° C. as $AlCl_3$ (108.98 g, 0.82 moles) was added slowly as a solid under a nitrogen flow over a 20 minute period of time. The reaction was then allowed to stir at 0° C. for 1 hour and then for 16 hours at 20° C. After the reaction period the mixture was poured on crushed ice and then filtered through diatomaceous earth (Celite™ brand). The mixture was then extracted with 1 M HCl (2×100 mL), 1 M $NaHCO_3$ (1×100 mL), and $H_2O$ (1×100 mL) and the organic layer dried over $MgSO_4$. Filtration followed by removal of the volatiles resulted in the isolation of a yellow oil. Vacuum distillation resulted in the isolation of the desired product as a pale yellow oil (50.4 g, 89.9 percent yield).

Preparation of 2,3,4,6-Tetramethylindene 2,4,6-Trimethylindanone (30.0 g, 0.17 moles) was stirred in diethylether (300 mL) at 0° C. as MeMgI (0.24 moles, 80.00 mL of 3.0 M solution in diethylether) was added dropwise. This mixture was stirred for another 30 minutes at 0° C. and then at 20° C. for an additional 3 hours. After the reaction period the mixture was poured on crushed ice, acidified with HCl, and extracted with 1 M HCl (2×100 mL), 1 M $NaHCO_3$ (1×100 mL), and then $H_2O$ (1×100 mL). Drying over $MgSO_4$ followed by filtration and solvent removal resulted in the isolation of a light brown oil. Vacuum distillation resulted in the isolation of the desired product as a pale yellow oil (28.0 g, 94.3 percent yield).

Preparation of Lithium 2,3,4,6-Tetramethylindenide 2,3,4,6-Tetramethylindene (11.12 g, 64.52 mmol) was stirred in hexane (250 mL) as nBuLi (70 mmol, 28 mL of 2.5 M solution in hexane) was added slowly. This mixture was allowed to stir overnight. After the reaction period the desired product was isolated as an off-white solid via filtration and used without further purification or analysis (10.98 g, 95.5 percent yield).

Preparation of Dimethylsilyl(2,3,4-tetramethylindenyl)chloride

Lithium 2,3,4,6-trimethylindenide (10.98 g, 61.6 moles) in THF (50 mL) was added dropwise to a solution of $Me_2SiCl_2$ (25.4 g, 0.2 moles) in THF (50 mL) at 0° C. This mixture was then allowed to stir at 20° C. for 16 hours. After the reaction period the volatiles were removed and the residue extracted and filtered using hexane. Removal of the hexane resulted in the isolation of the desired compound as a pale yellow oil (16.1 g, 99.4 percent yield).

Preparation of Dimethylsilyl(2,3,4,6-tetramethylindenyl)(t-butylamine)

Dimethylsilyl(2,3,4,6-tetramethylindenyl)Cl (16.1 g, 60.8 mmol) was stirred in hexane (200 mL) as $NEt_3$ (6.51 g, 64.4 mmol) was added followed by t-butylamine (5.61 g, 76.8 mmol). This mixture was allowed to stir for 24 hours. After the reaction period the mixture was filtered and the desired product isolated as a pale yellow oil following the removal of the volatiles (18.24 g, 99.5 percent yield).

Preparation of Dilitium (N-t-Butylamido)(dimethyl) (2,3,4,6-tetramethylindenyl)silane In the drybox 7.4 g (25.4 mmol) of (N-t-Butylamino) (dimethyl) (2,3,4,6-tetramethylindenyl) silane was dissolved in 300 ml of hexane. To this solution 24.5 ml (70.6 mmol) of nBuLi (2.00 M) was added dropwise. Upon complete addition of the nBuLi the solution was stirred for 12 hours after which the solvent was removed under reduced pressure to give 7.79 g (100 percent yield) of a yellow-orange powder.

Preparation of [(N-t-Butylamido)(dimethyl)(2,3,4,6-tetramethylindenyl)silane] Titanium Dichloride In the drybox 9.21 g (24.8 mmol) of $TiCl_3(THF)_3$ was dissovled in 75 ml of THF. To this solution 7.79 g (24.8 mmol) of dilithium (N-t-Butylamido) (dimethyl)(2,3,4,6-tetramethylindenyl)silane was added as a solid while stirring. The solution was then stirred for 45 minutes. After this time period 3.45 g of $PbCl_2$ (12.4 mmol) was added and the solution stirred for 45 minutes. The THF was then removed under reduced pressure. The residue was then extracted with toluene, the solution filtered, and the toluene removed under reduced pressure. The residue was then triturated with hexane and the solution volume reduced whereupon a red precipitate was formed and collected via filtration and washed with cold hexane. The solid product was dried under vacuum to yield 5.63 g (53 percent yield) of product.

EXAMPLE 22

Preparation of [(N-t-Butylamido)(dimethyl)(2,3,4,6-tetramethylindenyl)silane] Titanium Dimethyl In the drybox .400 g of [(N-t-Butylamido)(dimethyl)(2, 3,4,6-tetramethylindenyl) silane]titanium dichloride (0.9 mmol) was suspended in 50 ml of $Et_2O$. To this suspension 0.67 ml of MeMgI (3.0 M) was added dropwise while stirring over a 20 minute period. After the addition MeMgI was completed, the solution was stirred for 40 minutes. Then the Et$_2$O was removed under reduced pressure and the residue extracted with hexane, the solution filtered, the filtrate evaporated to dryness under reduced pressure to give 0.28 g (77 percent yield) of product.

EXAMPLE 23

Preparation of [(N-cyclohexylamido)(dimethyl)(2,3,4,6-tetramethylindenyl)-silane]titanium Dimethyl Preparation of Dimethylsilyl(2,3,4,6-tetramethylindenyl)(cyclohexylamine)

Dimethylsilyl(2,3,4,6-tetramethylindenyl)Cl (9.95 g, 37.8 mmol) was stirred in hexane (200 mL) as NEt$_3$ (4.1 g, 40.6 mmol) was added followed by cyclohexylamine (4.05 g, 40.8 mmol). This mixture was allowed to stir for 24 hours at 20° C. After the reaction period the mixture was filtered and the desired product isolated as a pale yellow oil following the removal of the volatiles (10.98 g, 89.3 percent yield).

Preparation of Dilitium (N-cyclohexylamido) (dimethyl) (2,3,4,6-tetramethylindenyl)silane In the drybox 4.0 g (12.6 mmol) of (N-cyclohexylamino) (dimethyl) (2,3,4,6-tetramethylindenyl) silane was dissolved in 300 ml of hexane. To this solution 12.6 ml (25.2 mmol) of nBuLi (2.00 M) was added dropwise at 20° C. Upon complete addition of the nBuLi the solution was stirred for 12 hours after which the solvent was removed under reduced pressure to give 4.12 g (96 percent yield) of a yellow-orange powder.

Preparation of [(N-cyclohexylamido)(dimethyl)(2,3,4,6-tetramethylindenyl)silane] Titanium Dichloride In the drybox 4.63 g (12.5 mmol) of TiCl$_3$(THF)$_3$ was dissolved in 75 ml of THF. To this solution 4.12 g (12.5 mmol) of dilithium (N-cyclohexylamido) (dimethyl)(2,3,4,6-tetramethylindenyl)silane was added as a solid while stirring at 20° C. The solution was then stirred for 45 minutes. After this time period 1.73 g of PbCl$_2$ (6.25 mmol) was added and the solution stirred for 45 minutes. The THF was then removed under reduced pressure. The residue was then extracted with toluene, the solution filtered, and the toluene removed under reduced pressure. The residue was then triturated with hexane and the solution volume reduced whereupon a red precipitate was formed and collected via filtration and washed with cold (0° C.) hexane. The solid product was dried under vacuum to yield 1.70 g (31 percent yield) of product.

EXAMPLE 24

Preparation of [(N-cyclohexylamido)(dimethyl)(2,3,4,6-tetramethylindenyl)silane]titanium Dimethyl In the drybox 0.300 g of [(N-t-cyclohexylamino) (dimethyl)(2,3,4,6-tetramethylindenyl) silane]titanium dichloride (0.675 mmol) was suspended in 50 ml of Et$_2$O at 20° C. To this suspension 0.45 ml of MeMgI (3.0 M) was added dropwise while stirring over a 20 minute period. After the addition MeMgI was completed, the solution was stirred for 40 minutes. Then the Et$_2$O was removed under reduced pressure and the residue extracted with hexane, the solution filtered, the filtrate evaporated to dryness under reduced pressure to give 0.27 g (100 percent yield) of product.

EXAMPLE 25

Preparation of [(N-t-Butylamido)(dimethyl)(2-propylindenyl)silane]titanium(II)-(1,4-diphenyl-1,3-butadiene)

In a 100 ml flask 0.500 g of (N-t-butylamido)(dimethyl) (2-propylindenyl)silane]titanium dichloride (1.23 mmol, from Example 12) was stirred with 0.225 g of 1,4-diphenyl-1,3-butadiene (1.23 mmol) in 70 ml of hexane. To this solution 1.0 ml of 2.5M nBuLi (in hexane) was added and the mixture refluxed for 1h. After cooling the solution to room temperature, the solution was filtered. The filter residue was then washed with hexane. The hexane was then removed from the filtrate under reduced pressure to give 0.460 g (69 percent yield) of product.

EXAMPLE 26

Preparation of [(N-cyclohexylamido)(dimethyl)(2,3-methylindenyl)silane]-titanium(II)(1,4-diphenyl-1,3-butadiene)

In a 100 ml flask 0.300 g of (N-cyclohexylamido) (dimethyl)(2,3-methylindenyl)silane)titanium dichloride (0.720 mmol, from Example 23) was stirred with 0.149 g of 1,4-diphenyl-1,3-butadiene (0.720 mmol) in 70 ml of hexane at 0° C. To this solution 0.577 ml of 2.5M nBuLi (in hexane) was added and the mixture refluxed for 2h. After cooling the solution to 20° C., the solution was filtered. The filter residue was then washed with hexane. The hexane was then removed from the filtrate under reduced pressure to give 0.109 g (27 percent yield) of product.

Polymerization Runs

A two-liter Parr reactor was charged with 740 g of mixed alkanes solvent (Isopar™-E) and 118 g of 1-octene comonomer. Hydrogen was added as a molecular weight control agent by differential pressure expansion from an ~75 ml addition tank at 25 psi (2070 Kpa). The reactor was heated to the polymerization temperature of 140° C. and saturated with ethylene at 500 psig (3.4 Mpa). 2.0 mmol each of catalyst and cocatalyst at 0.005M solutions in toluene were premixed in the drybox. After the desired premix time, the solution was transferred to a catalyst addition tank and injected into the reactor. The polymerization conditions were maintained for 15 minutes with ethylene on demand. The resulting solution was removed from the reactor, and a hindered phenol anti-oxidant (Irganox™ 1010 from Ciba Geigy Corp.) was added to the resulting solution. Polymers formed were dried in a vacuum oven set at 120° C. for about 20 hours. Results are contained in Table 2

TABLE 2

| Catalyst | Cocatalyst | Melt Index |
| --- | --- | --- |
| Example 22[1] | B(C$_6$F$_5$)$_3$ | 0.67 |
| Example 22 | " | 0.49 |
| Example 24[2] | " | 0.40 |
| Example 24 | " | 0.46 |
| Example 25[3] |  | 1.54 |

[1][(N-t-Butylamido)(dimethyl)(2,3,4,6-tetramethylindenyl)silane]Titanium Dimethyl
[2][(N-cyclohexylamido)(dimethyl)(2,3,4,6-tetramethylindenyl)silane] Titanium Dimethyl
[3][(N-t-Butylamino)(dimethyl)(2-propylindenyl)silane]titanium (1,4-diphenyl-1,3-butadiene)

EXAMPLE 27

Preparation of [(N-isopropylamido)(dimethyl)(2,3,4,6-tetramethylindenyl)silane] Titanium Dimethyl Preparation of Dimethylsilyl(2,3,4,6-tetramethylindenyl)(isopropylamine)

Dimethylsilyl(2,3,4,6-tetramethylindenyl)Cl (22.29 grams, 84.17 mmol) was stirred in THF as i-PrNH$_2$ (28.68 mL, 336.7 mmol) was added. The mixture was stirred for 16 hours. The volatiles were removed under reduced pressure. The residue was extracted with hexane and filtered through a diatomaceous earth filter aid on a 10–15 mm glass frit. The hexane was removed under reduced pressure to afford the product as a yellow oil. Yield; 17.23 grams, 71 percent.

Preparation of [(N-isopropylamido)(dimethyl)(2,3,4, 6-tetramethylindenyl)silane]titanium Dichloride In the drybox 17.23 grams (59.93 mmol) of dimethylsilyl (2,3,4,6-tetramethylindenyl)(isopropylamine) was dissolved in 350 mL of hexane in a 500 mL round-bottom schlenk flask. Tow equivalents of n-BuLi (47.94 mL, 2.5 M in hexanes) were then added via syringe. The reaction was stirred for twelve hours. The solvent was removed under reduced pressure to afford a orange powder. The powder was dissolved in 250 mL of THF. $TiCl_3(THF)_3$ (22.2 grams, 59.93 mmol) was added as a solid. After 15 minutes, $CH_2Cl_2$ (2.48 mL, 29.97 mmol) was added. After two hours, the solvent was removed under reduced pressure. The residue was extracted with toluene and filtered through a diatomaceous earth filter aid on a 10–15 mm glass frit. The toluene was removed under reduced pressure. The residue was slurried in hexane and filtered over a 10–15 mm glass frit. The residue was dried under reduced pressure to afford a red powder. Yield; 12.3 grams, 51 percent.

Preparation of [(N-isopropylamido)(dimethyl)(2,3,4, 6-tetramethylindenyl)silane]titanium Dimethyl In the drybox, [(N-isopropylamido)(dimethyl)(2,3,4,6-tetramethylindenyl)silane]titanium dichloride (6.92 grams, 17.12 mmol) was suspended in 150 mL of $Et_2O$ in a 250 mL round bottom flask. Two equivalents of a 3.0 M THF solution of MeMgCl (11.41 mL, 34.23 mmol) were added. The mixture was stirred for one hour. The volatiles were removed under reduced pressure. The residue was extracted with hexane and filtered through a diatomaceous earth filter aid on a 10–15 mm glass frit. The hexane was removed under reduced pressure to afford a orange powder. Yield; 5.8 grams, 93 percent.

EXAMPLE 28

Preparation of [(N-isopropylamido)(dimethyl)(2,3,4, 6-tetramethylindenyl)silane]titanium (1,4-diphenyl-1,3-butadiene)

In the drybox, 0.50 grams (1.24 mmol) of [(N-isopropylamido)(dimethyl)(2,3,4,6-tetramethylindenyl) silane] titanium dichloride was slurried in 60 mL of cyclohexane in a 100 mL round-bottom schlenk flask. 1,4-Diphenyl-1,3-butadiene (0.255 grams, 1.24 mmol) was added as a solid. Two equivalents of n-BuLi (0.989 mL, 2.5 M in hexanes) were then added via syringe. The flask was fitted with a condenser and heated to reflux for one hour. Upon cooling, the reaction was filtered through a diatomaceous earth filter aid (Celite™) on a 10–15 mm glass frit. The salts and filter aid were washed with 50 mL of pentane. The solvent was removed under reduced pressure to afford a red/brown powder. Yield; 300 mg, 45 percent.

Polymerization

Polymerization experiments were performed using a 3.8 liter stirred reactor charged with 1440 g of Isopar E™ (mixed alkanes; available from Exxon Chemicals Inc.), 132 g of 1-octene, and 10 mMol of hydrogen. The reactor was heated to 130° C. and saturated with ethylene to 450 psig (4.5 Mpa). The catalyst was prepared in a drybox by syringing together 5.0 mmol (1.0 mL, 0.005 M) of the metal complex, 15.0 mmol (1.0 mL, 0.015 M) of cocatalyst, trispentafluorophenylborane (TPFPB), and 50.0 mmol (1.0 mL, 0.05 M) of modified scavenger, methylaluminoxane (from Akzo-Nobel), with additional Isopar E™ to give a total volume of 17 mL. The catalyst solution was then transferred by syringe to a catalyst addition loop and injected into the reactor over approximately 4 minutes using a flow of high pressure solvent. The polymerization was allowed to proceed for 10 minutes while feeding ethylene on demand to maintain a pressure of 445 psig (4.5 Mpa). The polymer solution was then poured from the reactor into a nitrogen-purged glass kettle containing approximately 15 mL of isopropanol. A 20 mL aliquot of a stabilizer solution prepared by dissolving 6.66 g of Irgaphos™ 168 and 3.33 g of Irganox™ 1010 in 500 mL of toluene was added. The polymer solution was poured into a tray, air dried overnight, then thoroughly dried in a vacuum oven for two days. Results of polymerizations using the metal complexes of the invention and a comparative are contained in Table 3

TABLE 3

| Run | Complex | Cocatalyst | MI (dg/min)[3] |
|---|---|---|---|
| 1 | Ex. 27 | TPFPB[2] | 0.25 |
| 2 | Ex.28 | " | 0.22 |
| 3* | TTTD[1] | " | 4.8 |

*Comparative, not an example of the invention.
[1.]-(tetramethylcyclooentadienyl)dimethyl(t-butylamido)silanetitanium dimethyl
[2.]-trispentafluorophenylborane
[3.]-melt index, $I_2$, of the polymer measured in accordance with ASTM D-1238 (190/2.16)

As may be seen by comparison of the above results, the catalysts according to the present invention produce a polymer product that has a significantly lower melt index under comparable conditions, thereby signifying a significantly greater catalytic activity unded comparative polymerization conditions.

What is claimed is:

1. A metal complex corresponding to the formula:

wherein:
M is titanium, zirconium or hafnium in the +3 or +4 formal oxidation state;
A' is a substituted indenyl group substituted in at least the 2 or 3 position with a group selected from hydrocarbyl, fluoro-substituted hydrocarbyl, hydrocarbyloxy-substituted hydrocarbyl, dialkylamino-substituted hydrocarbyl, silyl, germyl and mixtures thereof, said group containing up to 40 nonhydrogen atoms, and said A' further being covalently bonded to M by means of a divalent Z group;
Z is divalent moiety bound to both A' and M via σ-bonds, said Z comprising boron, or a member of Group 14 of the Periodic Table of the Elements, and also comprising nitrogen, phosphorus, sulfur or oxygen;
X is an anionic or dianionic ligand group having up to 60 atoms exclusive of the class of ligands that are cyclic, delocalized, π-bound ligand groups;
X' independently each occurrence is a neutral Lewis base ligating compound, having up to 20 atoms;

p is 1 or 2, and is two less than the formal oxidation state of M, with the proviso that when X is a dianionic ligand group, p is 1; and q is 0, 1 or 2.

2. A metal complex according to claim 1 corresponding to the formula:

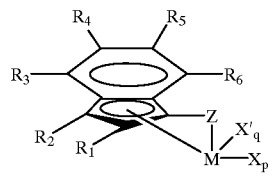

wherein:

R$_1$ and R$_2$, independently are groups selected from hydrogen, hydrocarbyl, perfluoro substituted hydrocarbyl, silyl, germyl and mixtures thereof, said group containing up to 20 nonhydrogen atoms, with the proviso that at least one of R$_1$ or R$_2$ is not hydrogen;

R$_3$, R$_4$, R$_5$, and R$_6$ independently are groups selected from hydrogen, hydrocarbyl, perfluoro substituted hydrocarbyl, silyl, germyl and mixtures thereof, said group containing up to 20 nonhydrogen atoms;

M is titanium, zirconium or hafnium;

Z is a divalent moiety comprising boron, or a member of Group 14 of the Periodic Table of the Elements, and also comprising nitrogen, phosphorus, sulfur or oxygen, said moiety having up to 60 non-hydrogen atoms;

p is 1 or 2;

q is zero or one;

with the proviso that:

when p is 2, q is zero, M is in the +4 formal oxidation state, and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)phosphino-substituted derivatives thereof, said X group having up to 20 nonhydrogen atoms, and when p is 1, q is zero, M is in the +3 formal oxidation state, and X is a staiblizing anionic ligand group selected from the group consisting of allyl, 2-(N,N-dimethylaminomethyl)phenyl, and 2-(N,N-dimethyl)-aminobenzyl, or M is in the +4 formal oxidation state, and X is a divalent derivative of a conjugated diene, M and X together forming a metallocyclopentene group.

3. A metal complex according to claim 1 corresponding to the formula:

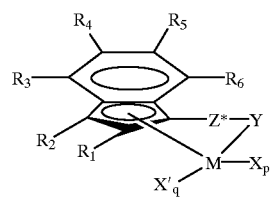

wherein:

R$_1$ and R$_2$ independently are hydrogen or C$_{1-6}$ alkyl, with the proviso that both R$_1$ and R$_2$ are not hydrogen;

R$_3$, R$_4$, R$_5$, and R$_6$ are independently hydrogen or C$_{1-6}$ alkyl;

M is titanium;

Y is —O—, —S—, —NR*—, —PR*—;

Z* is SiR*$_2$, CR*$_2$, SiR*$_2$SiR*$_2$, CR*$_2$, CR*=CR*, CR*$_2$SiR*$_2$, or GeR*$_2$;

R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* groups from Z (when R* is not hydrogen), or an R* group from Z and an R* group from Y form a ring system;

p is 1 or 2;

q is zero or one;

with the proviso that:

when p is 2, q is zero, M is in the +4 formal oxidation state, and X is independently each occurrence methyl or benzyl, and when p is 1, q is zero, M is in the +3 formal oxidation state, and X is 2-(N,N-dimethyl)aminobenzyl; or M is in the +4 formal oxidation state and X is 1,4-butadienyl.

4. A coordination polymerization catalyst comprising a metal complex according to claims 1, 2 or 3 and an activating cocatalyst.

5. A coordination polymerization catalyst according to claim 4 wherein the activating cocatalyst comprises trispentafluorophenyl-borane.

6. A coordination polymerization process comprising contacting one or more C$_{2-20}$ α-olefins under polymerization conditions with a catalyst comprising a metal complex according to claims 1, 2 or 3 and an activating cocatalyst.

7. A coordination polymerization process according to claim 6 wherein ethylene, propylene and optionally a non-conjugated diene are copolymerized.

8. A coordination polymerization process according to claim 7 which is a gas phase, solution or slurry polymerization.

9. A metal complex corresponding to the formula:

wherein:

M is titanium in the +2 formal oxidation state;

A' is a substituted indenyl group substituted in at least the 2 or 3 position with a group selected from hydrocarbyl, fluoro-substituted hydrocarbyl, hydrocarbyloxy-substituted hydrocarbyl, dialkylamino- substituted hydrocarbyl, silyl, germyl and mixtures thereof, said group containing up to 40 nonhydrogen atoms, and said A' further being convalently bonded to M by means of a divalent Z group;

Z is a divalent moiety bound to both A' and M via σ-bonds, said Z comprising boron, or a member of Group 14 of the Periodic Table of the Elements, and also comprising nitrogen, phosphorus, sulfur or oxygen; and X' is a neutral Lewis base ligating compound, having up to 20 atoms.

10. A metal complex corresponding to the formula:

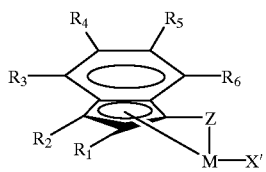

wherein:
- $R_1$ $R_2$, independently are groups selected from hydrogen, hydrocarbyl, perfluoro substituted hydrocarbyl, silyl, germyl and mixtures thereof, said group containing up to 20 nonhydrogen atoms, with the proviso that at least one of $R_1$ or $R_2$ is not hydrogen;
- $R_3$, $R_4$, $R_5$, and $R_6$ independently are groups selected from hydrogen, hydrocarbyl, perfluoro substituted hydrocarbyl, silyl, germyl and mixtures thereof, said group containing up to 20 nonhydrogen atoms;
- M is titanium;
- Z is a divalent moiety comprising boron, or a member of Group 14 of the Periodic Table of the Elements, and also comprising nitrogen, phosphorus, sulfur or oxygen, said moiety having up to 60 non-hydrogen atoms; and
- X' is a neutral, conjugated or nonconjugated diene, optionally substituted with one or more hydrocarbyl groups, said X' having up to 40 carbon atoms and forming a π-complex with M.

11. a metal complex according to claim 9 corresponding to the formula:

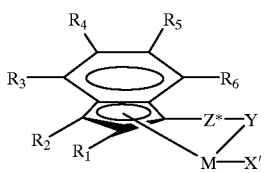

wherein:
- $R_1$ and $R_2$ independently are hydrogen or $C_{1-6}$ alkyl, with the proviso that both $R_1$ and $R_2$ are not hydrogen;
- $R_3$, $R_4$, $R_5$, and $R_6$ are independently hydrogen or $C_{1-6}$ alkyl;
- M is titanium;
- Y is —O—, —S—, —NR*—, —PR*—;
- Z* is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$;
- R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* gropus from Z (when R* is not hydrogen), or an R* group from Z and an R* group from Y form a ring system; and
- X' is 1,4-diphenyl-1,3-butadiene or 1,3-pentadiene.

12. A coordination polymerization catalyst comprising a metal complex according to claims 9, 10 or 11 and an activating cocatalyst.

13. A coordination polymerization catalyst according to claim 12 wherein the activating cocatalyst comprises tris(pentafluorophenyl)borane.

14. A coordination polymerization process comprising contacting one or more $C_{2-20}$ α olefins under polymerization conditions with a catalyst comprising a metal complex according to claims 9, 10 or 11 and an activating cocatalyst.

15. A process according to claim 14 which is a gas phase, solution or slurry polymerization.

16. A process according to claim 14 wherein ethylene, propylene and optionally a nonconjugated diene are copolymerized.

17. A coordination polymerization process comprising contacting one or more $C_{2-20}$ α olefins under polymerization conditions with a catalyst comprising an activating cocatalyst and a metal complex corresponding to the formula:

wherein:
- M is titanium in the +2, +3 or +4 formal oxidation state;
- A' is a substituted indenyl group substituted in at least the 2 or 3 position with a group selected from hydrocarbyl, fluoro-substituted hydrocarbyl, hydrocarbyloxy-substituted hydrocarbyl, dialkylamino- substituted hydrocarbyl, silyl, germyl and mixtures thereof, said group containing up to 40 nonhydrogen atoms, and said A' further being covalently bonded to M by means of a divalent Z group;
- Z is a divalent moiety bound to both A' and M via σ-bonds, said Z comprising boron, or a member of Group 14 of the Periodic Table of the Elements, and also comprising nitrogen, phosphorus, sulfur or oxygen;
- X is an anionic or dianionic ligand group having up to 60 atoms exclusive of the class of ligands that are cyclic, delocalized, π-bound ligand groups;
- X' independently each occurrence is a neutral Lewis base ligating compound, having up to 20 atoms;
- p is 0, 1 or 2, and is two less than the formal oxidation state of M, with the proviso that when X is a dianionic ligand group, p is 1; and
- q is 0, 1 or 2;

and the activating cocatalyst comprises an alumoxane and trispentafluorophenylborane in a molar ratio from 1:1 to 5:1.

18. A coordination polymerization process comprising contacting one or more $C_{2-20}$ α olefins under polymerization conditions with an activating cocatalyst and a catalyst comprising a metal complex corresponding to the formula: hydrocarbyl groups, said X' having up to 40 carbon atoms and forming a π-complex with M, and the activating cocatalyst comprises an alumoxane and tris(pentafluorophenyl)borane in a molar ratio from 1:1 to 5:1.

19. A process according to claim 18, wherein the metal complex corresponds to the formula:

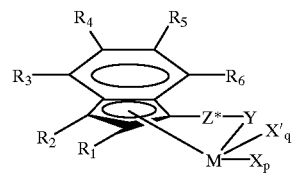

wherein:
- $R_1$ and $R_2$ independently are hydrogen or $C_{1-6}$ alkyl, with the proviso that both $R_1$ and $R_2$ are not hydrogen;

$R_3$, $R_4$, $R_5$, and $R_6$ ar independently hydrogen or $C_{1-6}$ alkyl;

M is titanium;

Y is —O—, —S—, —NR*—, —PR*—;

Z* is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$;

R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* groups from Z (when R* is not hydrogen), or an R* group from Z and an R* group from Y form a ring system;

p is 0, 1 or 2;

q is zero or one;

with the proviso that:

when p is 2, q is zero, M is in the +4 formal oxidation state, and X is independently each occurrence methyl or benzyl, when p is 1, q is zero, M is in the +3 formal oxidation state, and X is 2-(N,N-dimethyl)aminobenzyl; or M is in the +4 formal oxidation state and X is 1,4-butadienyl, and

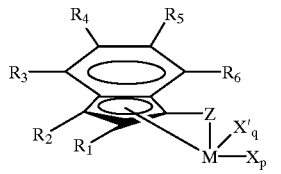

wherein:

$R_1$ $R_2$, independently are groups selected from hydrogen, hydrocarbyl, perfluoro substituted hydrocarbyl, silyl, germyl and mixtures thereof, said group containing up to 20 nonhydrogen atoms, with the proviso that at least one of $R_1$ or $R_2$ is not hydrogen;

$R_3$, $R_4$, $R_5$, and $R_6$ independently are groups selected from hydrogen, hydrocarbyl, perfluoro substituted hydrocarbyl, silyl, germyl and mixtures thereof, said group containing up to 20 nonhydrogen atoms;

M is titanium, zirconium or hafnium;

Z is a divalent moiety comprising boron, or a member of Group 14 of the Periodic Table of the Elements, and also comprising nitrogen, phosphorus, sulfur or oxygen, said moiety having up to 60 non-hydrogen atoms;

p is 0, 1 or 2;

q is zero or one;

with the proviso that:

when p is 2, q is zero, M is in the +4 formal oxidation state, and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)phosphino-substituted derivatives thereof, said X group having up to 20 nonhydrogen atoms, when p is 1, q is zero, M is in the +3 formal oxidation state, and X is a stabilizing anionic ligand group selected from the group consisting of allkyl, 2-(N,N-dimethylaminomethyl)phenyl, and 2-(N,N-dimethyl)-aminobenzyl, or M is in the 30 4 formal oxidation state, and X is a divalent derivative of a conjugated diene, M and X together forming a metallocyclopentene group, and when p is 0, q is 1, M is in the +2 formal oxidation state, and X' is a neutral, conjugated or nonconjugated diene, optionally substituted with one or more when p is 0, q is 1, M is in the +2 formal oxidation state, and X' is 1,4-diphenyl-1,3-butadiene or 1,3-pentadiene.

20. A process according to claim 17 which is a gas phase, solution or slurry polymerization.

21. A process according to claim 17 wherein ethylene, propylene and optionally a nonconjugated diene or copolymerized.

* * * * *

UNITED STATES PATENT AND TRADEMARK OFFICE
CERTIFICATE OF CORRECTION

PATENT NO : 6,015,868

DATED : Jan. 18, 2000

INVENTOR(S) : Peter N. Nickias et al.

It is certified that error appears in the above-identified patent and that said Letters Patent are hereby corrected as shown below:

Column 54, line 6, the second occurrence of "$CR^*_2$" should correctly read --$CR^*_2CR^*_2$--.

Column 54, line 42, "claim 7" should correctly read --claim 6--.

Column 55, line 32, "a metal" should correctly read --A metal--.

Column 57, lines 25-43, through column 58, lines 1-34, should be deleted from claim 19 and inserted into claim 18, column 56, line 49, following "formula:".

Column 58, line 22, "or" should correctly read --are--.

Signed and Sealed this

Twenty-fourth Day of April, 2001

*Attest:*

NICHOLAS P. GODICI

*Attesting Officer*     *Acting Director of the United States Patent and Trademark Office*